(12) United States Patent
Lou et al.

(10) Patent No.: US 6,462,046 B2
(45) Date of Patent: Oct. 8, 2002

(54) HETEROCYCLE DERIVATIVES AS PPAR-GAMMA AGONISTS

(75) Inventors: Boliang Lou, Louisville, KY (US); Adnan M. M. Mjalli, Jamestown, NC (US)

(73) Assignee: Advanced SynTech, LLC, Louisville, KY (US)

( * ) Notice: Subject to any disclaimer, the term of this patent is extended or adjusted under 35 U.S.C. 154(b) by 0 days.

(21) Appl. No.: 09/734,458

(22) Filed: Dec. 11, 2000

(65) Prior Publication Data

US 2002/0082263 A1 Jun. 27, 2002

Related U.S. Application Data

(63) Continuation-in-part of application No. 09/478,743, filed on Jan. 6, 2000, now abandoned.

(51) Int. Cl.[7] ............... A61K 31/496; C07D 241/08; C07D 401/12
(52) U.S. Cl. ............... 514/253.01; 514/235.8; 544/121; 544/360; 544/383; 544/390
(58) Field of Search .......... 514/235.8, 253.01, 514/255.01; 544/121, 360, 390, 383

(56) References Cited

FOREIGN PATENT DOCUMENTS

WO          98/37079    *  8/1998

OTHER PUBLICATIONS

STN International R CAPLUS Database, Accession No. 1977:5424; Singh et al. Indian J. Chem., Sect. B 14B(7), 532–5 (1976), abstract.*

* cited by examiner

Primary Examiner—Ceila Chang
Assistant Examiner—Sonya Wright
(74) Attorney, Agent, or Firm—John E. Vanderburgh

(57) ABSTRACT

Compounds having the structure

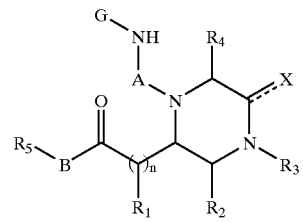

are peroxisome proliferator-activated receptor-gamma (PPAR-gamma) selective agonists and as such are useful in the modulation of blood glucose and the increase of insulin sensitivity in mammals. This activity of the piperazine derivatives of the invention make them particularly useful in the treatment of those conditions selected from the group consisting of diabetes, atherosclerosis, hyperglycemia, hyperlipidemia, obesity, syndrome X, insulin resistance, hypertension, heart failure and cardiovascular disease in mammals.

14 Claims, No Drawings

HETEROCYCLE DERIVATIVES AS PPAR-GAMMA AGONISTS

This application is a CIP of Ser. No. 09/478,743 filed Jan. 6, 2000 now abandoned.

FIELD OF THE INVENTION

The present invention relates to novel compounds, pharmaceutical compositions containing them, to processes for their preparation and to the uses thereof. More particularly, this invention relates to compounds that exhibit agonist activity to peroxisome proliferator-activated receptor gamma enabeling them to be useful in modulation of blood glucose and the increase of insulin sensitivity in mammals

BACKGROUND OF THE INVENTION

Type II or Non-Insulin Dependent Diabetes Mellitus (NIDDM) involves abnormal glucose metabolism characterized by defects in three organ systems, namely, liver (increased glucose production by the liver due to increased levels of glucagon and free fatty acids as well as recycling of gluconeogenic precursors lactate and pyruvate), pancreas (impaired glucose-induced insulin secretion leading to fasting hyperglycemia) and peripheral target tissues such as the skeletal muscle (resistance to the action of insulin due to insulin receptor or post receptor defects).

The sulfonyl urea class of drugs exert their antihyperglycemic effects by stimulating the release of insulin from the β cells of the pancreas. These however have undesirable toxic effects such as fatigue of β cells with long term use, obesity and incidence of hypoglycemia. The biguanides act on insulin resistance by reduced glucose absorption, decreased glucuneogenesis, increased anorexia, enhance insulin binding to its receptor and increased glucose transport in fat and muscle. Thus the treatment of insulin resistance and/or suppression of increased hepatic glucose production in type II diabetes is an attractive area of drug development.

The thiazolidinedione class of drugs (troglitazone), was developed for its potent lipid-peroxide-lowering activity which improved hyperglycemia, hyperinsulinemia and hypertriglceridemia in the diabetic KK mice (a genetically insulin resistance model of type II diabetes). Troglitazone also increased glucose uptake in adipocytes thus increasing insulin sensitivity and responsiveness.

Three cell lines have been used to assess the effects of thiazolidinediones: NIH 3T3 mouse fibroblast that differentiates into insulin responsive adipocytes (fat cell model), HepG2, a human hepatoma cell line (liver cell model) and L6 rat myocytes (muscle cell model). In the first model the "glitazones" increase the differentiation into adipocytes and increase the expression of fat cell-specific genes like lipoprotein lipase, aP2, acyl CoA synthase and adipsin thereby contributing to the stimulation of triglyceride clearance. In the latter model and in fat cells the thiazolidinediones increase the expression of glucose transporter, GLUT4, thereby exerting an insulin-sensitizing effect by stimulating basal and insulin-stimulated glucose uptake. Recently, it has been demonstrated that the thiazolidinediones and prostanoids of the J2 series are ligands for the Peroxisome Proliferator Activated Receptors (members of the steroid/thyroid hormone receptor super family). Members of this family include the alpha, gamma and delta, of which the PPARg receptor has been shown to be preferentially expressed in preadipocytes and immune system. A general model for activation of PPARgamma by thiazolidinediones include a ligand induced conformational change leading to the displacement of a "corepressor" or allowing the binding of a coactivator thereby facilitating heterodimerization with another nuclear receptor RXR. The activated heterodimer interacts with specific DNA sequences "TGACCT-N-TGACCT" or PPREs (the Peroxisome Proliferator Response Elements) to activate transcription of thiazolidinedione responsive genes (such as lipoprotein lipase), either directly or by interacting with sites that overlap insulin responsive sequences (IRS) (such as in the glucokinase promoter). The PPREs have been identified in the promoters of a number of genes for proteins involved in the regulation of lipid metabolism suggesting that PPARgamma is an attractive therapeutic target for obesity and NIDDM.

SUMMARY OF THE INVENTION

The present invention relates to heterocycle derivatives which are peroxisome proliferator-activated receptor-gamma (PPAR-gamma) selective agonists and such are useful in the modulation of blood glucose and the increase of insulin sensitivity in mammals. This activity of the piperazine derivatives of the invention make them particularly useful in the treatment of those conditions selected from the group consisting of diabetes, atherosclerosis, hyperglycemia, hyperlipidemia, obesity, syndrome X, insulin resistance, hypertension, heart failure and cardiovascular disease in mammals.

DESCRIPTION OF THE INVENTION

The present invention relates to the compounds of formula (I) below and its derivatives, pharmaceutically acceptable salts thereof, which are non-thiazolidinedione PPAR-gamma agonists so that they might surmount the problems associated with the known thiazolidinediones and thus offer an advantage as a therapeutic agent in treating diseases described above.

The present invention provides novel compounds of Formula (I) or pharmaceutical

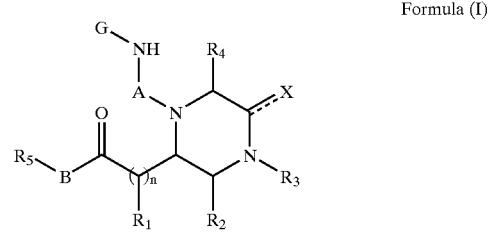

Formula (I)

acceptable salts thereof, wherein the broken line represents an optional double bond;

X is H, O, S;

A is —C(O)—, —S(O)m—;

B is O, S, $NR_6$, wherein $R_6$ is H, $C_1$–$C_6$ alkyl, $C_2$–$C_6$ alkenyl and $C_2$–$C_6$ alkynyl and $C_3$–$C_6$ cycloalkyl;

n is 0 or 1;

m is 1 or 2;

G is $C_3$–$C_{10}$ cycloalkyl, $C_4$–$C_{10}$ cycloalkenyl, saturated $C_3$–$C_{10}$ heterocyclyl, $C_3$–$C_{10}$ cycloalkyl-$C_1$–$C_3$ alkyl, $C_4$–$C_{10}$ cycloalkenyl-$C_1$–$C_3$ alkyl, saturated $C_3$–$C_{10}$ heterocyclyl-$C_1$–$C_3$ alkyl, said cycloalkyl, cycloalkenyl, heterocyclyl and alkyl optionally substituted with 1 to 3 groups of $R_s$, wherein heterocyclyl contains 1 to 4 heteroatoms which may be nitrogen, sulfur or oxygen atom;

$R_1$ is hydrogen, hydroxy, thio, nitro, cyano, azido, amino, trifluoromethyl, trifluoromethoxy, $C_1$–$C_6$ alkyl, $C_1$–$C_6$ alkyloxy, $C_1$–$C_6$ alkylthio, $C_1$–$C_6$ alkylamino, $C_1$–$C_6$ alkenyl, $C_1$–$C_6$ alkenyloxy, $C_1$–$C_6$ alkenylamino, $C_3$–$C_8$ cycloalkyl, $C_3$–$C_8$ cycloalkyloxy, $C_3$–$C_8$ cycloalkylamino, $C_3$–$C_8$ cycloalkylthio, $C_1$–$C_6$ alkylcarbonylamino, $C_3$–$C_8$ cycloalkylcarbonylamino, $C_5$–$C_{10}$ aryl, $C_5$–$C_{10}$ heteroaryl or $C_5$–$C_{10}$ saturated heteroaryl; said aryl, heteroaryl, alkyl, alkenyl, and cycloalkyl optionally substituted with 1 to 3 groups of $R_s$;

$R_2$, $R_3$, $R_4$ and $R_5$ independently are H, trifluoromethyl, $C_5$–$C_{10}$ aryl, $C_5$–$C_{10}$ heteroaryl, $C_1$–$C_{10}$ alkyl, $C_2$–$C_{10}$ alkenyl, $C_2$–$C_{10}$ alkynyl, $C_3$–$C_{10}$ cycloalkyl, saturated $C_5$–$C_{10}$ heteroaryl, $C_5$–$C_{10}$ aryl-$C_1$–$C_{10}$ alkyl, $C_5$–$C_{10}$ heteroaryl-$C_1$–$C_{10}$ alkyl, $COR_7$, $CO_2R_7$, $CONR_7R_8$, $SO_2NR_7R_8$, said aryl, heteroaryl, alkyl, alkenyl, and cycloalkyl optionally substituted with 1 to 3 groups of $R_s$;

$R_7$ and $R_8$ independently are H, hydroxy, $C_1$–$C_{10}$ alkyl, $C_2$–$C_{10}$ alkenyl, $C_2$–$C_{10}$ alkynyl, $C_3$–$C_{10}$ cycloalkyl, $C_5$–$C_{10}$ aryl, $C_5$–$C_{10}$ heteroaryl, said aryl, heteroaryl, alkyl, alkenyl, and cycloalkyl optionally substituted with 1 to 3 groups of $R_s$;

$R_s$ represents a member selected from the group consisting of halo, cyano, nitro, trihalomethyl, carbamoyl, hydroxy, $OCF_3$ acyl, aryl, heteroaryl, $S(O)R_8$, $=N(OR_8)$, $SO_2R_8$, $COOR_8$, $—CONR_7R_8$, $—C_1$–$C_6$alkylCONR$_7$R$_8$, $C_1$–$C_6$alkyloxy, aryloxy, arylC$_1$–C$_6$alkyloxy, thio, $C_1$–C$_6$alkylthio, arylthio, arylC$_1$–C$_6$alkylthio, NR$_7$R$_8$, $C_1$–C$_6$alkylamino, arylamino, arylC$_1$–C$_6$alkylamino, di(arylC$_1$–C$_6$alkyl) amino, $C_1$–C$_6$alkylcarbonyl, arylC$_1$–C$_6$alkylcarbonyl, $C_1$–C$_6$alkylcarboxy, arylC$_1$–C$_{C6}$alkylcarboxy, $—NR_7CO_2R_8$, $—NR_7CO_2R_8$, $—NR_7SO_2R_8$, $—CONR_7R_8$, $—SO_2NR_7R_8$, $—OCONR_7R_8$, $—C_1$–C$_6$alkylaminoCONR$_7$R$_8$, arylC$_1$–C$_6$alkylcarbonylamino, tetrahydrofuryl, morpholinyl, piperazinyl, or a saturated or partial saturated cyclic 5,6 or 7 membered amine or lactam; said aryl, and heteroaryl optionally substituted with 1 to 3 groups of halo or $C_1$–C$_6$alkyl; wherein $R_7$ and $R_8$ are defined as above.

Definitions

As used herein, the "—" (e.g. —COR$_7$ which indicates the carbonyl attachment point to the scaffold) signifies a stable covalent bond, certain preferred points of attachment points being apparent to those skilled in the art.

The term "halogen" or "halo" include fluorine, chlorine, bromine, and iodine.

The term "alkyl" includes $C_1$–$C_{12}$ saturated aliphatic hydrocarbon groups unless otherwise defined. It may be straight or branched alkyl groups. Branched means that one or more lower alkyl groups such as methyl, ethyl, or propyl are attached. The alkyl group may be substituted by one or more hydroxy, halo, cycloalkyl, cycloalkenyl or heterocyclyl. Examplary alkyl groups include methyl, ethyl, fluoromethyl, difluoromethyl, trifluoromethyl, cyclopropylmethyl, cyclopentylmethyl, n-propyl, i-propyl, n-butyl, t-butyl, n-pentyl, 3-pentyl, heptyl, octyl, nonyl, decyl, and the like.

When substituted alkyl is present, this refers to a straight, branched or cyclic alkyl group as defined above, substituted with 1–3 groups as defined with respect to each variable.

The term "alkenyl" includes $C_2$–$C_{12}$ aliphatic hydrocarbon groups containing at least one carbon to carbon double bond and which may be straight or branched unless otherwise defined. Preferably one carbon to carbon double bond is present, up to four non-aromatic carbon to carbon double bond may present. Branched means one or more lower alkyl groups such as methyl, ethyl or propyl are attached to a linear alkenyl chain. "Lower alkenyl" means about 2 to about 4 carbon atoms in the chain which may be straight or branched. For example, this definition shall include but is not limited to ethenyl, propenyl, butenyl, and cyclohexylbutenyl, decenyl, and the like. As described above with respect to alkyl, the straight, branched and cyclic portion of the alkenyl group may contain double bonds and may be substituted when substituted alkenyl group is provided.

The term "alkynyl" includes $C_2$–$C_{12}$ aliphatic hydrocarbon groups containing at least one carbon to carbon triple bond and which may be straight or branched unless otherwise defined. Preferably one carbon to carbon double bond is present, up to carbon to carbon triple bond may present. Branched means one or more lower alkyl groups such as methyl, ethyl or propyl are attached to a linear alkynyl chain. "Lower alkynyl" means about 2 to about 4 carbon atoms in the chain which may be straight or branched. For example, this definition shall include but is not limited to ethynyl, propynyl, butynyl, and the like. As described above with respect to alkyl, the straight, branched and cyclic portion of the alkynyl group may contain triple bonds and may be substituted when substituted alkynyl group is provided.

The term "cycloalkyl" means a non-aromatic mono- or multicyclic ring system of about 3 to about 10 atoms. Preferred monocyclic cycloalkyl rings include cyclopentyl, fluorocyclopentyl, cyclohexyl and halocyclohexyl and cycloheptyl; More preferred is cyclohexyl. The cycloalkyl group may be substituted by one or more halo, methylene ($CH_2=$), alkyl, fused aryl and fused heteroaryl.

The term "cycloalkenyl" means a non-aromatic mono- or multicyclic ring system containing a carbon-carbon double bond and having about 3 to about 10 atoms. Preferred monocyclic cycloalkyl rings include cyclopentenyl, cyclohexenyl and halocyclohexenyl and cycloheptenyl; More preferred is cyclohexenyl. The cycloalkyl group may be substituted by one or more halo, methylene ($CH_2=$), alkyl, fused aryl and fused heteroaryl.

The term "heterocyclyl" means an about 4 to about 10 member monocyclic or multicyclic ring system wherein one or more of the atoms in the ring system is an element other than carbon chosen amongst nitrogen, oxygen or sulfur. The heterocyclyl may be optionally substituted by one or more alkyl group substituents. Examplary heterocyclyl moieties include quinuclidine, pentamethylenesulfide, tetrahedropyranyl, tetrahydrothiophenyl, pyrrolidinyl or tetrahydrofuranyl.

The term "alkyloxy" (e.g. methoxy, ethoxy, propyloxy, allyloxy, cyclohexyloxy) represents an "alkyl" group as defined above having the indicated number of carbon atoms attached through an oxygen bridge. The term "alkyloxyalkyl" represents an "alkyloxy" group attached through an alkyl group as defined above having the indicated number of carbon atoms.

The term "aryloxy" (e.g. phenoxy, naphthyloxy and the like) represents an aryl group as defined below attached through an oxygen bridge.

The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through a sulfur bridge.

The term "alkyloxycarbonyl" (e.g. methylformate, ethylformiat and the like) represents and "alkyloxy" group as defined above attached through a carbonyl group.

The term "aryloxycarbonyl" (e.g. phenylformate, 2-thiazolylformiat and the like) represents an "aryloxy" group as defined above attached through a carbonyl group.

The term "arylalkyloxycarbonyl" (e.g. benzylformate, phenylethylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexylthio and the like) represents an "alkyl" group as defined above having the indicated number of carbon atoms attached through a sulfur bridge.

The term "arylalkylthio" (e.g. phenylmethylthio, phenylethylthio, and the like) represents an "arylalkyl" group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl) propylamino, pyrrolidinyl, piperidinyl, and the like) represents one or two "alkyl" groups as defined above having the indicated number of carbon atoms attached through an amine bridge. The two alkyl groups may be taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, $NRR_8$, $C_1$–$C_6$alkylamino$C_1$–$C_6$alkyl substituent wherein the alkyl and aryl groups are optionally substituted as defined in the definition section and R and $R_8$ are defined as above.

The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a cyclic or bicyclic system containing 3 to 11 carbon atoms and 0 to 2 additional heteroatoms selected from nitrogen, oxygen or sulfur, the ring system can optionally be substituted with at least one $C_1$–$C_6$alkyl, aryl, aryl$C_1$–$C_6$alkyl, hydroxy, $C_1$–$C_6$alkyloxy, $C_1$–$C_6$alkyloxy$C_1$–$C_6$alkyl, $NRR_8$, $C_1$–$C_6$alkylamino$C_1$–$C_6$alkyl substituent wherein the alkyl and aryl groups are optionally substituted as defined in the definition section and $R_7$ and $R_8$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above.

The term "alkylcarbonyl" (e.g. cyclooctylcarbonyl, pentylcarbonyl) represents an "alkyl" group as defined above having the indicated number of carbon atoms attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonylalkyl" represents an "arylalkylcarbonyl" group attached through an alkyl group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonylaminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an "alkylcarbonylaminoalkyl" group attached through a carbonyl group. The nitrogen atom may be further substituted with an "alkyl" or "aryl" group.

The term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art. Aryl thus contains at least one ring having at least 5 atoms, with up to two such rings being present, containing up to 10 atoms therein, with alternating (resonating) double bonds between adjacent carbon atoms. Aryl groups may likewise be substituted with 0–3 groups selected from $R_s$. The definition of aryl includes but is not limited to phenyl, biphenyl, indenyl, fluorenyl, naphthyl (1-naphtyl, 2-naphthyl).

Heteroaryl is a group containing from 5 to 10 atoms, 1–4 of which are heteroatoms, 0–4 of which heteroatoms are nitrogen, and 0–1 of which are oxygen or sulfur, said heteroaryl groups being substituted with 0–3 groups selected from $R_s$. The definition of heteroaryl includes but is not limited to pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isopuinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydrobenzo[b]furanyl (2-(2,3-dihydrobenzo[b]furanyl), 3-(2,3-dihydrobenzo[b]furanyl), 4-(2,3-dihydrobenzo[b]furanyl), 5-(2,3-dihydrobenzo [b]furanyl), 6-(2,3-dihydrobenzo[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydrobenzo[b]thiophenyl (2-(2,3-dihydrobenzo [b]thiophenyl), 3-(2,3-dihydrobenzo[b]thiophenyl), 4-(2,3-dihydrobenzo[b]thiophenyl), 5-(2,3-dihydrobenzo[b]-thiophenyl), 6-(2,3-dihydrobenzo[b]thiophenyl), 7-(2,3-dihydrobenzo[b]thiophenyl)), indolyl (1-indolyl, 2-indolyl, 3-indolyl, 4-indolyl, 5-indolyl, 6-indolyl, 7-indolyl), indazolyl (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepinyl (5H-dibenz[b,f]azepin-1-yl, 5H-dibenz[b,f]azepin-2-yl, 5H-dibenz[b,f]azepin-3-yl, 5H-dibenz[b,f]azepin-4-yl, 5H-dibenz[b,f]azepie-5-yl), 10,11-dihydro-5H-dibenz[b,f]azepinyl (10,11-dihydro-5H-dibenz[b,f]azepin-1-yl, 10,11-dihydro-5H-dibenz[b,f] azepin-2-yl, 10,11-dihydro-5H-dibenz[b,f]azepin-3-yl, 10,11-dihydro-5H-dibenz[b,f]azepin-4-yl, 10,11-dihydro-5H-dibenz[b,f]azepin-5-yl), piperidinyl (2-piperidinyl, 3-piperidinyl, 4-piperidinyl), pyrrolidinyl (1-pyrrolidinyl, 2-pyrrolidinyl, 3-pyrrolidinyl), phenylpyridyl (2-phenylpyridyl, 3-phenylpyridyl, 4-phenylpyridyl), phenylpyrimidinyl (2-phenylpyrimidinyl, 4-phenylpyrimidinyl, 5-phenylpyrimidinyl, 6-phenylpyrimidinyl), phenylpyrazinyl, phenylpyridazinyl (3-phenylpyridazinyl, 4-phenylpyridazinyl, 5-phenylpyridazinyl).

The tern "arylcarbonyl" (e.g. 2-thiophenylcarbonyl, 3-methoxyanthrylcarbonyl, oxazolylcarbonyl) represents an "aryl" group as defined above attached through a carbonyl group.

The term "arylalkylcarbonyl" (e.g. (2,3-dimethoxyphenyl)propylcarbonyl, (2-chloronaphthyl) pentenylcarbonyl, imidazolylcyclopentylcarbonyl) represents an "arylalkyl" group as defined above wherein the "alkyl" group is in turn attached through a carbonyl.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of formula 1, where a basic or acidic group is present in the structure, are also included within the scope of this invention. When an acidic substituent is present, such as —COOH or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, acetate, oxalate, maleate, fumarate, citrate, palmoate, methanesulfonate, p-toluenesulfonate, and the like, can be used as the dosage form.

Also, in the case of the —COOH or —P(O)(OH)$_2$ being present, pharmaceutically acceptable esters can be employed (e.g. methyl, tert-butyl, pivaloyloxymethyl, and the like), and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other.

Prefered compounds for use according to the invention are selected from the following species:

Methyl[1-cyclohexylcarbamoyl-4-benzyl-6-(S)-isobutyl-5-oxo-piperazin-2-yl]-acetate;
[1-Cyclohexylcarbamoyl-4-benzyl-6-(S)-isobutyl-5-oxo-piperazin-2-yl]-acetic acid;
N-Tetrahydrofurfuryl[1-cyclohexylcarbamoyl-4-benzyl-6-(S)-isobutyl-5-oxo-piperazin-2-yl]-acetamide;
N-Methyl[1-cyclohexylcarbamoyl-4-(3,5-dimethoxybenzyl)-6-(S)-isobutyl-piperazin-2-yl]-acetamide;
[1-Cyclohexylcarbamoyl-4-benzyl-6-(S)-benzyl-5-oxo-piperazin-2-yl]-acetic acid;
N-Methyl[1-cyclohexylcarbamoyl-4-benzyl-6-(S)-benzyl-5-oxo-piperazin-2-yl]-acetamide;
N-Methyl[1-cyclohexylcarbamoyl-4-(4-methoxybenzyl)-6-(S)-methylcarbamoyl-3-oxo-piperazin-2-yl]-acetamide;
N-Tetrahydrofurfuryl(R)-[1-cyclohexylcarbamoyl-4-(3,5-dimethoxybenzyl)-6-(S)-isobutyl-5-oxo-piperazin-2-yl]-acetamide;
N-Tetrahydrofurfuryl(S)-[1-cyclohexylcarbamoyl-4-(3,5-dimethoxybenzyl)-6-(S)-isobutyl-5-oxo-piperazin-2-yl]-acetamide;

N-Tetrahydrofurfuryl(R)-[1-cyclohexylcarbamoyl-4-cyclohexylmethyl-6-(S)-isobutyl-5-oxo-piperazin-2-yl]-acetamide;
N-Tetrahydrofurfuryl(S)-[1-cyclohexylcarbamoyl-4-cyclohexylmethyl-6-(S)-isobutyl-5-oxo-piperazin-2-yl]-acetamide;
N-Butyl(R)-[1-cyclohexylcarbamoyl-4-(3-pyridylmethyl)-6-(S)-isobutyl-5-oxo-piperazin-2-yl]-acetamide;
N-Butyl(S)-[1-cyclohexylcarbamoyl-4-(3-pyridylmethyl)-6-(S)-isobutyl-5-oxo-piperazin-2-yl]-acetamide;
N-Butyl(R)-[1-cyclohexylcarbamoyl-4-(3,4-dimethoxybenzyl)-6-(S)-isobutyl-5-oxo-piperazin-2-yl]-acetamide;
N-Butyl(S)-[1-cyclohexylcarbamoyl-4-(3,4-dimethoxybenzyl)-6-(S)-isobutyl-5-oxo-piperazin-2-yl]-acetamide;
[1-cyclohexylcarbamoyl-4-(3,4-dimethoxybenzyl)-6-(S)-isobutyl-5-oxo-piperazin-2-yl]-acetic acid;
(R)-[1-cyclohexylcarbamoyl-4-(3,4-dimethoxybenzyl)-6-(S)-isobutyl-5-oxo-piperazin-2-yl]-acetic acid;
(S)-[1-cyclohexylcarbamoyl-4-(3,4-dimethoxybenzyl)-6-(S)-isobutyl-5-oxo-piperazin-2-yl]-acetic acid;
N-Methyl(R)-[1-(1-piperidylcarbamoyl)-4-(3,4-dimethoxybenzyl)-6-(S)-isobutyl-5-oxo-piperazin-2-yl]-acetamide;
N-Methyl(S)-[1-(1-piperidylcarbamoyl)-4-(3,4-dimethoxybenzyl)-6-(S)-isobutyl-5-oxo-piperazin-2-yl]-acetamide;
N-Tetrahydrofurfuryl(R)-[1-cyclohexylcarbamoyl-4-(3,4-dimethoxybenzyl)-6-(S)-isobutyl-5-oxo-piperazin-2-yl]-acetamide;
N-Tetrahydrofurfuryl(S)-[1-cyclohexylcarbamoyl-4-(3,4-dimethoxybenzyl)-6-(S)-isobutyl-5-oxo-piperazin-2-yl]-acetamide;
N-Tetrahydrofurfuryl(R)-[1-cyclohexylcarbamoyl-4-(4-dimethylminobenzyl)-6-(S)-isobutyl-5-oxo-piperazin-2-yl]-acetamide;
N-Tetrahydrofurfuryl(S)-[1-cyclohexylcarbamoyl-4-(4-dimethylminobenzyl)-6-(S)-isobutyl-5-oxo-piperazin-2-yl]-acetamide;
Methyl[1-cyclohexylcarbamoyl-4-(3,5-dimethoxybenzyl)-6-(S)-isobutyl-5-oxo-piperazin-2-yl]-acetate;
N-Methyl(R)-[1-cyclohexylmethylcarbamoyl-4-(3,5-dimethoxybenzyl)-6-(S)-isobutyl-5-oxo-piperazin-2-yl]-acetamide;
N-Methyl(S)-[1-cyclohexylmethylcarbamoyl-4-(3,5-dimethoxybenzyl)-6-(S)-isobutyl-5-oxo-piperazin-2-yl]-acetamide;
N-Methyl(R)-[1-cyclohexylcarbamoyl-4-benzyl-6-(S)-isobutyl-5-oxo-piperazin-2-yl]-acetamide;
N-Methyl(S)-[1-cyclohexylcarbamoyl-4-benzyl-6-(S)-isobutyl-5-oxo-piperazin-2-yl]-acetamide;
N-Methyl(R)-[1-cyclopentylcarbamoyl-4-(3,5-dimethoxybenzyl)-6-(S)-isobutyl-5-oxo-piperazin-2-yl]-acetamide;
N-Methyl(S)-[1-cyclopentylcarbamoyl-4-(3,5-dimethoxybenzyl)-6-(S)-isobutyl-5-oxo-piperazin-2-yl]-acetamide;
N-Methyl[1-cyclohexylcarbamoyl-4-(3,5-dimethoxybenzyl)-6-(S)-isobutyl-5-oxo-piperazin-2-yl]-acetamide;
N-Methyl(R)-[1-cyclohexylcarbamoyl-4-(3,5-dimethoxybenzyl)-6-(S)-isobutyl-5-oxo-piperazin-2-yl]-acetamide;
N-Methyl(S)-[1-cyclohexylcarbamoyl-4-(3,5-dimethoxybenzyl)-6-(S)-isobutyl-5-oxo-piperazin-2-yl]-acetamide;
N-Butyl[1-cyclohexylcarbamoyl-4-(3,5-dimethoxybenzyl)-6-(S)-isobutyl-5-oxo-piperazin-2-yl]-acetamide;
N-Butyl(R)-[1-cyclohexylcarbamoyl-4-(3,5-dimethoxybenzyl)-6-(S)-isobutyl-5-oxo-piperazin-2-yl]-acetamide;
N-Butyl(S)-[1-cyclohexylcarbamoyl-4-(3,5-dimethoxybenzyl)-6-(S)-isobutyl-5-oxo-piperazin-2-yl]-acetamide;
N-Butyl(R)-[1-cyclohexylcarbamoyl-4-cyclohexylmethyl-6-(S)-isobutyl-5-oxo-piperazin-2-yl]-acetamide;
N-Butyl(S)-[1-cyclohexylcarbamoyl-4-cyclohexylmethyl6-(S)-isobutyl-5-oxo-piperazin-2-yl]-acetamide;
N-Methyl[1-cyclohexylcarbamoyl-4-cyclohexylmethyl-6-(S)-isobutyl-5-oxo-piperazin-2-yl]-acetamide;
N-Methyl[1-cyclohexylcarbamoyl-4-(3,5-dimethoxybenzyl)-6-(S)-butyl-5-oxo-piperazin-2-yl]-acetamide;
N-Ethyl[1-cyclohexylcarbamoyl-4-(3,5-dimethoxybenzyl)-6-(S)-isobutyl-5-oxo-piperazin-2-yl]-acetamide;
N-(2-Hydroxyethyl)[1-cyclohexylcarbamoyl-4-(3,5-dimethoxybenzyl)-6-(S)-isobutyl-5-oxo-piperazin-2-yl]-acetamide;

Preparation of Compounds

Compounds of formula 1 may be prepared by the application or adaptation of known methods, by which is meant methods used heretofore or described in the literature. General methods for preparing compounds according to the invention may also be prepared as described in the schemes that follows.

Scheme 1 illustrated below, refers to the preparation of compounds of the formula (1), wherein n=1, and $R_3$ is introduced from the corresponding amine used in the first step. The compound of formula 1-2 is prepared from a compound of formula 1-1, a 4-bromocrotonate derivative which can be reacted with an amine in an appropriate solvent (such as dichloromethane, DMF, THF, etc.). The subsequent coupling with an Fmoc amino acids or a Boc

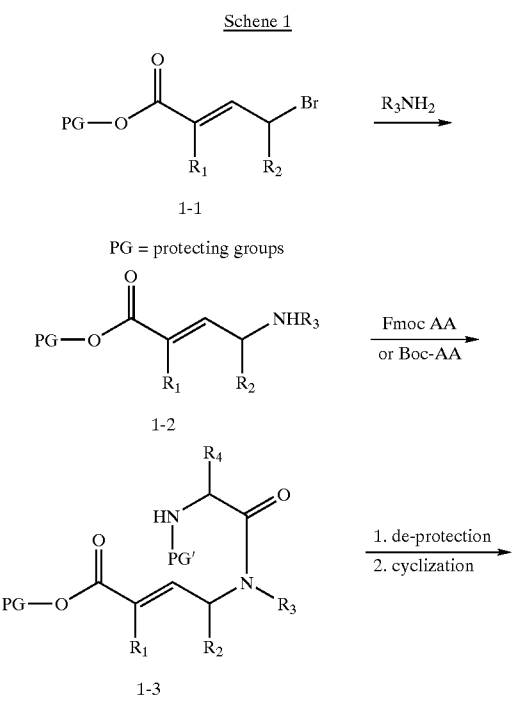

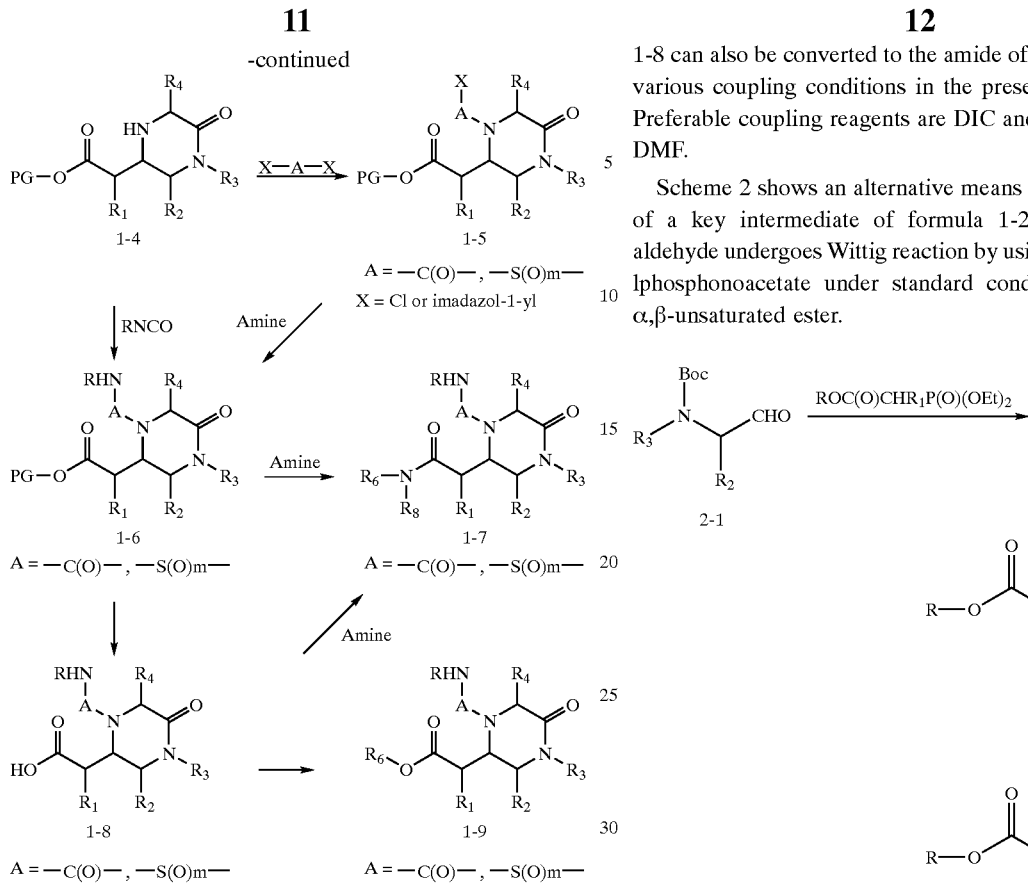

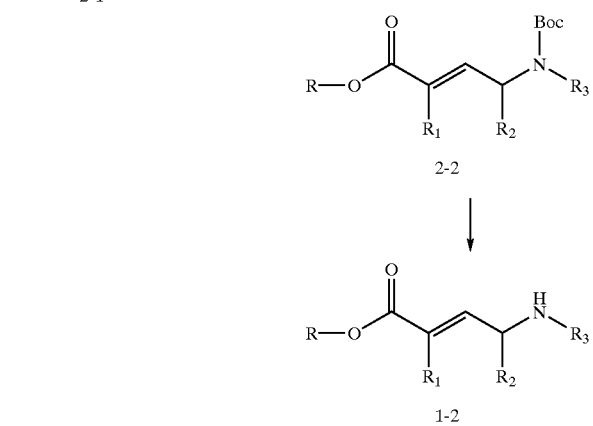

amino acid in the presence of DIC or EDC in a solvent, such as DMF, THF or dichloromethane, under the standard conditions gives an acylated product of formula 1-3. Removal of Fmoc protecting group can be achieved by the treatment with piperidine in DMF. A simultaneous cyclization occurs under the basic conditions to give the cyclic compounds, formula 1-4. Alternatively, Boc protecting group can be removed under the standard condition (TFA/DCM) gives a free amine derivative which then undergoes an intramolecular Michael addition in the presence of base, such as triethylamine or DIEA. Compounds of formula 1-6 are obtained by the treatment with various isocyanates in the presence of a base (DIEA, triethylamine, DMAP or pyridine).

Alternatively, the preparation of a compound of formula 1-6 from 1-4 is also achieved via an intermediate of formula 1-5 which is formed by the treatment with excess of phosgene, triphosgene, sulfonyl chloride, or their equivalents, such as carbonyldiimidazole and sulfonyldiimidazole. The subsequent formation of a urea or a sulfonamide is achieved by the treatment with an amine.

The compound of formula 1-6 is then converted to a carboxylic acid of formula 1-8 under various cleavage conditions, preferably in the presence of LiOH/THF/H$_2$O at room temperature for 15–24 h. A compound of formula 1-9 is prepared from the compound of formula 1-8 in the presence of an appropriate alcohol and a coupling reagent (DCC/DMAP, BOP-Cl/Et$_3$N) in an aprotic solvent at 20–30° C., preferably at room temperature. An amide of formula 1-7 is prepared from the compound of formula 1-6 in the presence of an excess of amine. The compound of formula 1-8 can also be converted to the amide of formula 1-7 under various coupling conditions in the presence of the amine. Preferable coupling reagents are DIC and EDC in DCM or DMF.

Scheme 2 shows an alternative means for the preparation of a key intermediate of formula 1-2. A Boc-α-amino aldehyde undergoes Wittig reaction by using an alkyl dialkylphosphonoacetate under standard conditions to give an α,β-unsaturated ester.

Removal of the Boc protecting group gives the intermediate 1-2.

Scheme 3 shows a sequence for preparation of the corresponding piperazine analogs described as formula 3-5, 3-6, and 3-7. A reductive amination of Boc-α-amino aldehyde gives a 1,2-diamine of formula 3-2. The unprotected amino group is alkylated with a 4-bromocrotonate to give a precursor 3-3. An intramolecular cyclization under the same conditions as described in

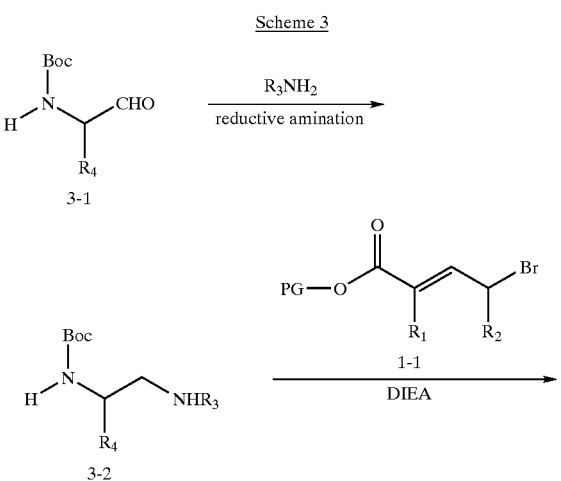

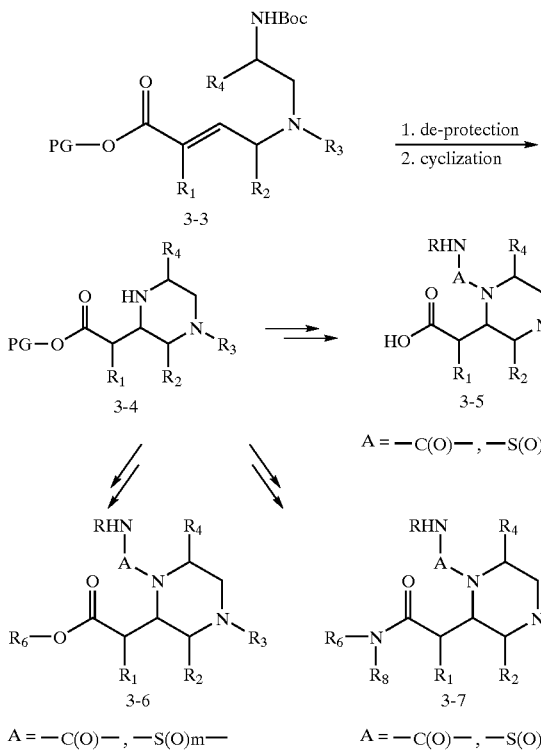

Scheme 1 gives a piperazine intermediate. The same precedure can be followed for the preparation of ureas and sulfonamides.

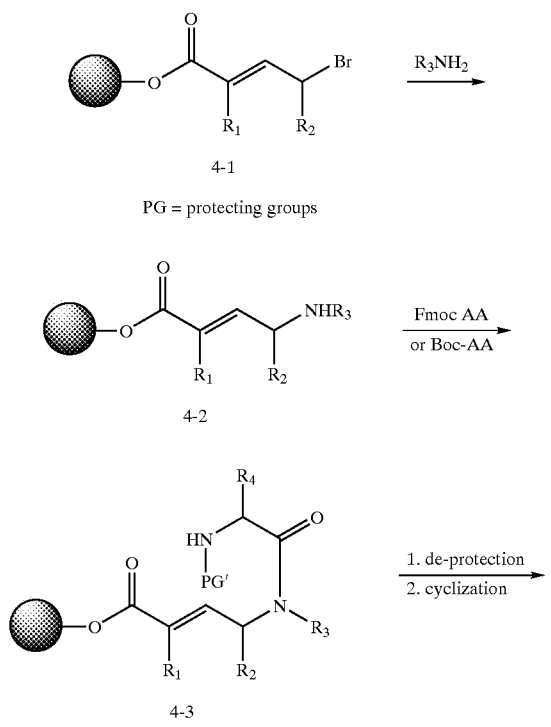

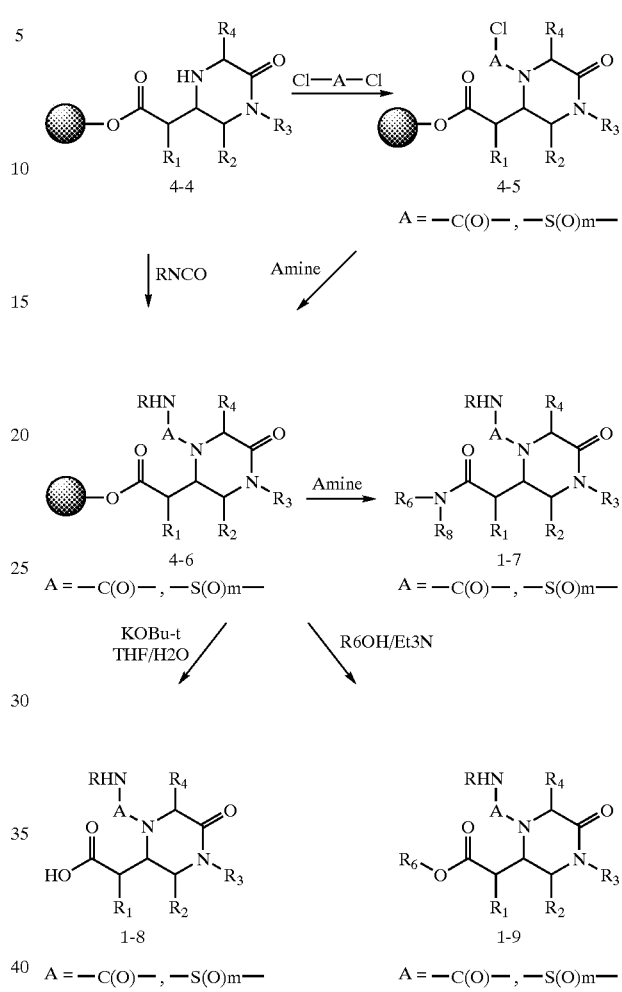

An alternative means for the preparation of these compounds according to the invention is the use of solid phase synthesis method. As shown in Scheme 4, a bromocrotonate moiety can be linked to a solid support, e.g, Wang resin, Merrifield resin, etc. Compared to the Scheme 1, the solid support can be considered as an alternative protecting group. However, a unique advantage of this approach is the intermediate from each step is not to be purified, the reaction can be pushed to completion by using the excess of the reagents (usually 5–10 equiv.). A final compound is released under an appropriate cleavage condition.

Scheme 5 shows a sequence for the preparation of a class of compounds described as formula 5-6. By the solid phase approach, An orthogonally protected Boc-Fmoc-diaminopropionate resin is selectively de-protected to release β-amino group. A reductive alkylation followed by acylation with fumaric acid monoester give a compound of formula 5-3.

Scheme 5

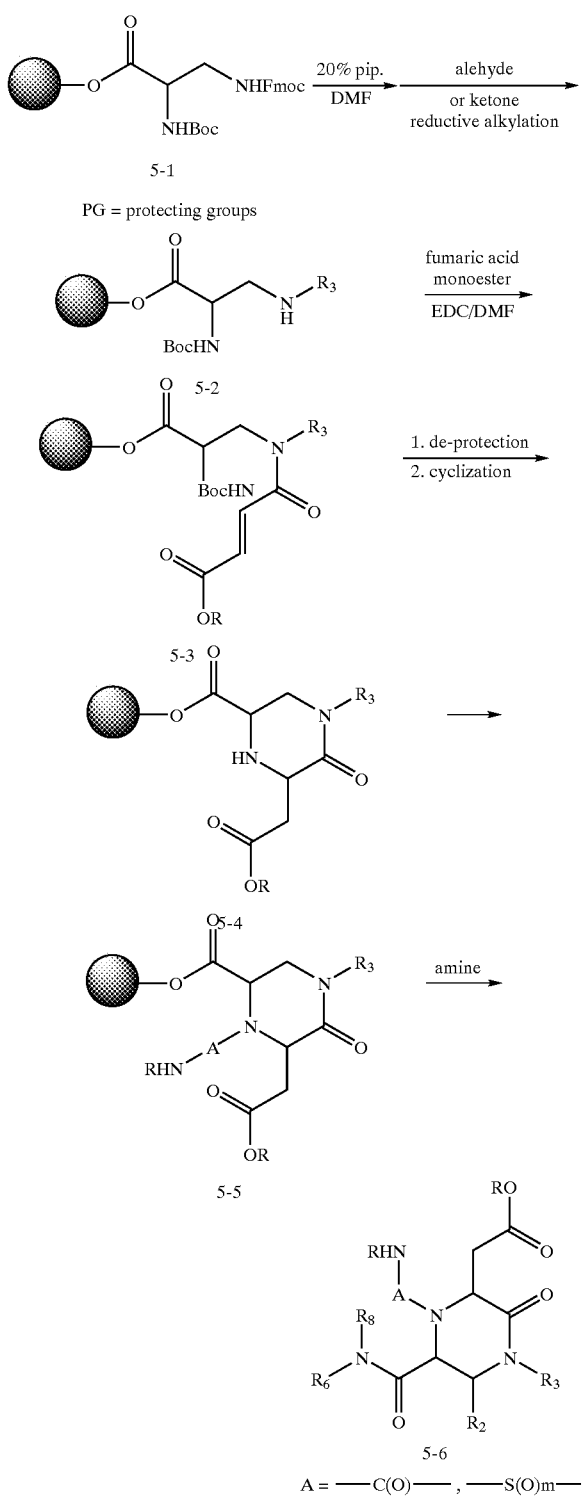

Removal of the Boc group followed by cyclization give a polymer-bound piperazinone intermediate of formula 5-4. The further functional groups, such as urea and sulfonamide, can be introduced under the same conditions described above.

EXAMPLES

The following examples are by way of illustration of various aspects of the present invention and are not intended to be limiting thereof.

General Procedures—Reagent Systems and Test Methods

Anhydrous solvents were purchased from Aldrich Chemical Company and used directly. Resins were purchased from Advanced ChemTech, Louisville, Ky., and used directly. The loading level ranged from 0.35 to 1.1 mmol/g. Unless otherwise noted, reagents were obtained from commercial suppliers and used without further purification. Preparative thin layer chromatography was preformed on silica gel pre-coated glass plates (Whatman PK5F, 150 Å, 1000 μm) and visualized with UV light, and/or ninhydrin, p-anisaldehyde, ammonium molybdate, or ferric chloride. NMR spectra were obtained on a Varian Mercury 300 MHz spectrometer. Chemical shifts are reported in ppm. Unless otherwise noted, spectra were obtained in $CDCl_3$ with residual $CHCl_3$ as an internal standard at 7.26 ppm. IR spectra were obtained on a Midac M1700 and absorbencies are listed in inverse centimeters. HPLC/MS analysis were performed on a Hewlett Packard 1100 with a photodiode array detector coupled to a Micros Platform II electrospray mass spectrometer. An evaporative light scattering detector (Sedex 55) was also incorporated for more accurate evaluation of sample purity. Reverse phase columns were purchased from YMC, Inc. (ODS-A, 3 μm, 120 Å, 4.0×50 mm).

Solvent system A consisted of 97.5% MeOH, 2.5% $H_2O$, and 0.05% TFA. Solvent system B consisted of 97.5% $H_2O$, 2.5% MeOH, and 0.05% TFA. Samples were typically acquired at a mobile phase flow rate of 2 ml/min involving a 2 minute gradient from solvent B to solvent A with 5 minute run times. Resins were washed with appropriate solvents (100 mg of resin/1 ml of solvent). Technical grade solvents were used for resin washing.

Examples 1–3

Preparation of methyl[1-cyclohexylcarbamoyl-4-benzyl-6-(S)-isobutyl-5-oxo-piperazin-2-yl]-acetate, [1-cyclohexylcarbamoyl-4-benzyl-6-(S)-isobutyl-5-oxo-piperazin-2-yl]-acelic acid, and N-tetrahydrofurfuryl[1-cyclohexylcarbamoyl-4-benzyl-6-(S)-isobutyl-5-oxo-piperazin-2-yl]-acetamide Example 1

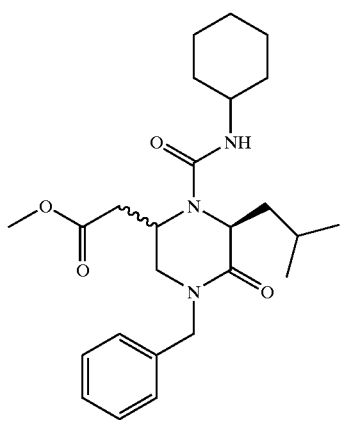

Example 2

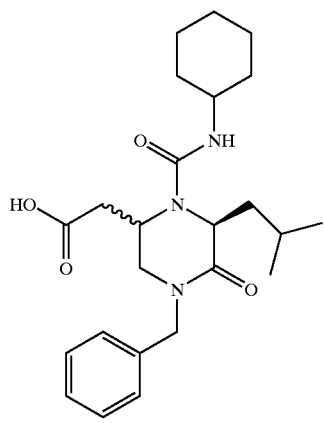

Example 3

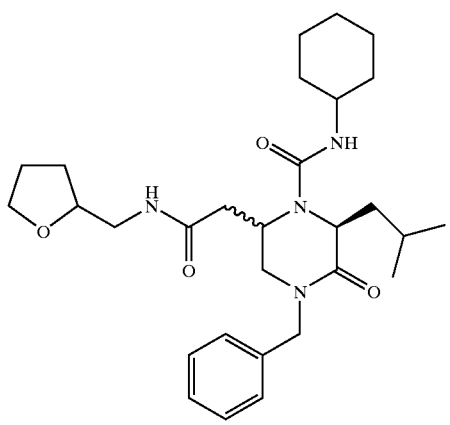

Substitution with Amine

To a solution cooled at 0 C. containing methyl 4-bromocrotonate (2 mL, 17 mmol) and DCM (25 mL) were added benzyl amine (2.2 mL, 20.4 mmol) and DIEA (5.9 mL, 34 mmol). The mixture was stirred at 0 C. for 10 min, then warmed to rt with continuing stirring for 2 h at which time TLC analysis indicated the starting material had been consumed. The mixture was then concentrated and the residue was treated with EtOAc. The solid was filtered and washed with EtOAc. The combined filtrates were concentrated to give the crude product.

Boc Protection

A half amount of the above crude product was treated with dioxane (10 mL), water (3 mL) and DIEA (2 mL). To this mixture was added $(Boc)_2O$ (1.8 g, 9 mmol). After vigorously stirring at rt for 2 h, TLC indicated the reaction was completed. The mixture was concentrated, diluted with EtOAc, washed with aqueous citric acid and with brine. The organic layer was dried over $Na_2SO_4$, filtered and concentrated to give a residue which was purified by flash chromatography on silica gel (1.6 g, 62% yield).

Acylation with an Amino Acid

Another half amount of the crude product obtained from the first step was added to a mixture of Fmoc-L-Leu-OH (3.5 g, 10 mmol) and DCM (20 mL). After the resulting mixture was cooled to 0 C., EDC (1.9 g, 10 mmol) was added. The mixture was stirred for 15 min, then warmed to room temperature with stirring for another 3 h. The mixture was diluted with EtOAc, washed with 1N HCl, water and brine. The organic layer was dried over $Na_2SO_4$. Filtration followed by concentration gave a residue which was purified by flash chromatography on silica gel (2.6 g, 56%). MS (ES) m/e: 541 (M+H$^+$).

Deprotection and Cyclization

The above Fmoc-Leu coupled product (1.08 g, 2 mmol) was treated with 5% piperidine in DCM for 30 min. The solution was concentrated, the residue was diluted with EtOAc, and then washed with $H_2O$. The organic layer was dried over $Na_2SO_4$. Filtration and concentration gave the crude cyclic product which was then dissolved in DCM (10 mL). Cyclohexyl isocyanate (500 mg, 4 mmol) was added. The mixture was stirred at rt for 2 h. Water was then added, the product was extracted with EtOAc. The organic layer was dried over $Na_2SO_4$, filtered and concentrated to give a residue. Purification by flash chromatography on silica gel gave the title compound (700 mg, 79% yield). MS (ES) m/e: 444 (M+H$^+$).

Hydrolysis of Methyl Ester

The methyl ester obtained in the above step (150 mg) was treated with 1.2 equiv. of LiOH in a 1:1 mixture of dioxane and water (5 mL). The mixture was stirred at rt until the methyl ester had been consumed. The mixture was then concentrated and another equiv. of LiOH in 5 mL of water was added. The aqueous layer was washed with $Et_2O$, then acidified by addition of a 1 N HCl solution. The product was extracted with EtOAc. The organic layer was washed with water, dried over $Na_2SO_4$. Filtration followed by concentration gave the pure product (100 mg). MS (ES) m/e: 430 (M+H$^+$).

Amide

The carboxylic acid obtained above (50 mg, 0.12 mmol) was dissolved in 1 mL of DCM. Tetrahydrofurfurylamine (20 mg, 0.2 mmol) and EDC (38.5 mg, 0.2 mmol) were added. The resulting mixture was stirred at rt for 12 h, then diluted with EtOAc, washed with 1 N HCl. The organic layer was then neutralized with sat. $NaHCO_3$ followed by washing with brine. Concentration under reduced pressure gave an oil which was purified by flash chromatography (hexane:EtOAc, 2:1–1:1) (45 mg, 89% yield). The product contains two diastereoisomers (cis and trans) which were separated on a preparative TLC plate. MS (ES) m/e: 513 (M+H$^+$).

Example 4

Preparation of N-methyl[1-cyclohexylcarbamoyl-4-(3,5-dimethoxybenzyl)-6-(S)-isobutyl-piperazin-2-yl]-acetamide

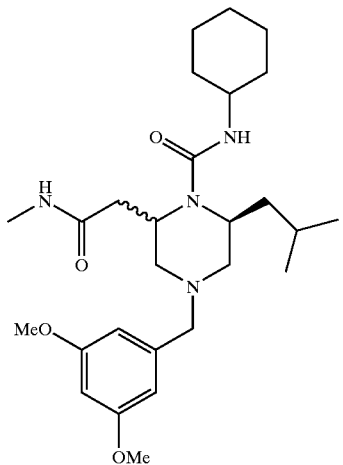

Reductive Amination

To a mixture of Boc-L-Leu-CHO (1.17 g, 5.5 mmol) in DCM (30 mL) were added trimethyl orthoformate (1.18 mL, 10.8 mmol), 3,5-dimethoxybenzylamine (1 g, 5.9 mmol) and a catalytic amount of HOAc (0.2 mL). The resulting mixture was stirred at rt for 4 h. The mixture was concentrated and dried in vacuo. The obtained imine was dissolved in 10 mL of MeOH. To this solution was added sodium cyanoborohydride (650 mg, 11 mmol). The resulting mixture was stirred at rt overnight, then poured into ice water with stirring for 5 min, extracted with EtOAc. The organic layer was washed with sat. NaHCO$_3$ and brine. Concentration gave the crude product which was purified by flash chromatography on silica gel (1.4 g, 70% yield).

N-alkylation with methyl 4-bromocrotonate

To a solution of the amine prepared above (366 mg, 1 mmol) and DIEA (258 mg, 2 mmol) in DCM (5 mL) cooled at 0 C. was added methyl 4-bromocrotonate (215 mg, 1.2 mmol). The mixture was stirred at 0 C. for 10 min, then warmed to rt. Stirring continued for 12 h at which time TLC analysis indicated the starting material had been consumed. The mixture was then concentrated and the residue was treated with EtOAc. The solid was filtered and washed with EtOAc. The combined filtrates were concentrated to give the crude product which was purified by flash chromatography on silica gel (250 mg, 54% yield). MS (ES) m/e: 465 (M+H$^+$).

De-protection and Cyclization

The obtained product from the previous step (100 mg) was treated with 20% TFA in DCM (0.5 mL) at rt for 15 min. The mixture was then evaporated to give a residue which was dissolved in DCM (5 mL). The solution was then washed with sat. NaHCO$_3$. DIEA (5 mmol) was added. After stirring for 30 min, the mixture was concentrated to give the crude cyclic product which was directly used for the next step without further purification. MS (ES) m/e: 365 (M+H$^+$).

Urea Formation and Aminolysis

The above crude product was dissolved in 2 mL of DCE, cyclohexyl isocyanate (50 mg, 0.4 mmol) was then added. After stirring at rt for 2 h, it was treated with 1 mL of water. The organic layer was separated and concentrated to give a residue which was treated with a 1:1 mixture of 40% MeNH$_2$ (aq.) and THF (1 mL). The mixture was stirred at rt for 12 h. Concentration followed by purification on a preparative TLC plate gave the pure compound (70 mg, 66% yield). MS (ES) m/e: 489 (M+H$^+$).

Example 5

Preparation of [1-cyclohexylcarbamoyl-4-benzyl-6-(S)-benzyl-5-oxo-piperazin-2-yl]-acetic acid Example 5

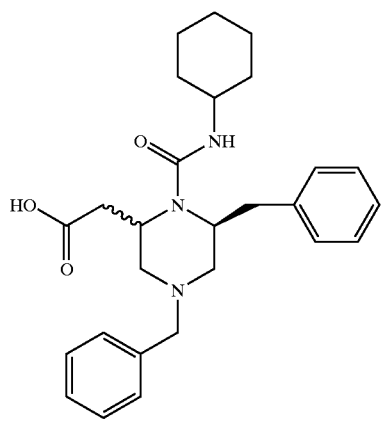

Step 1: Displacement of Bromide

4-Bromocrotonate Wang Resin (300 mg, loading 0.9 mmol/g) was suspended in a solution of benzylamine [0.5M] in NMP (8 mL) and shaken for 45 min at room temperature. After filtration, the resulting mixture was washed by 2×10 mL of DMF, 3×10 mL of DCM/MeOH, 2×10 mL of DCM then dried under nitrogen. IR(KBr): 1718 cm$^{-1}$.

Step 2: Acylation

To the resin were added Fmoc-L-phenylalanine (10 eq), DIC (10 eq), and DMF (3 mL/100 mg of resin). The resulting mixture was shaken for 24 h at room temperature. After filtration, the resin was washed with 2×DMF (3 mL/100 mg of resin), 2×DCM/MeOH, 2×DCM then dried under nitrogen.

Step 3: Deprotection and Cyclization

The resin was suspended in a solution of piperidine (20%) in DMF (3 mL/100 mg of resin) and shaken for 30 min. After filtration, the resin was washed with 2×DMF (3 mL/100 mg of resin), 2×DCM/MeOH, 2×DCM then dried under nitrogen. IR (KBr): 1734 cm$^{-1}$.

Step 4: Formation of Urea

The resin was suspended in a solution of cyclohexyl isocyanate [0.5M] in DCE (3 mL/100 mg of resin) and shaken for 12 h at room temperature. The resin was filtered and washed by 2×DME, 2×DCM/MeOH, 2×DCM then dried under nitrogen.

Alternative Method for the Formation of Urea

The resin was suspended in a solution of 0.1 M DIEA in DCE (1 mL/100 mg resin). A solution of 0.1 M triphosgene (0.5 mL/100 mg resin) was then added. After shaking at rt for 4 h, a solution of 1 M cyclohexylamine in DMF (0.3 mL) was added. Shaking continued overnight. The resin was filtered and washed with 2×DMF, 3×DCM/MeOH, 3×DCM then dried under nitrogen.

Step 5: Cleavage of the Product

The resin was suspended in a mixture of TFA (25%) in DCM (3 mL/100 mg of resin) and shaken for 30 min. After filtration, the resin was washed by 2×DCM (3 mL/100 mg of resin). The volatils were removed under reduced pressure to lead to crude 50 mg. Purification via the ester (treatment of the crude by TMSCH$_2$N$_2$) afforded 25 mg of pure desired compound as a mixture of two isomers with a 2:1 ratio (39%, based on 0.9 mmol/g loading). MS (ES) m/e (relative intensity): 478 (M+H$^+$, 100), 353 (40).

1H NMR (a mixture of two isomers of the corresponding methyl esters, CDCl$_3$) δ7.40–7.02 (m, 10H), 4.90 (d, 1H), 4.76 (d, 1H), 4.71 (dd, 1H), 4.55 (dd, 1H), 4.50 (m, 1H), 4.32 (d, 1H), 4.31 (d, 1H), 4.08 (d, 1H), 4.02 (m, 1H), 3.73 (m, 2H), 3.62 (m, 1H), 3.57 (s, 3H), 3.54 (dd, 1H), 3.48 (s, 3H), 3.43 (dd, 1H), 3.40 (dd, 1H), 3.19 (dd, 1H), 3.09 (dd, 1H), 3.04 (dd, 1H), 2.87 (dd, 1H), 2.48 (dd, 1H), 2.20 (m, 1H), 2.17 (dd, 1H), 1.97 (dd, 1H), 1.95–1.80 (m, 2H), 1.71–1.57 (m, 3H), 1.41–1.25 (m, 2H), 1.10 (m, 1H).

Example 6

Preparation of N-methyl[1-cyclohexylcarbamoyl-4-benzyl-6-(S)-benzyl-5-oxo-piperazin-2-yl]-acetamide

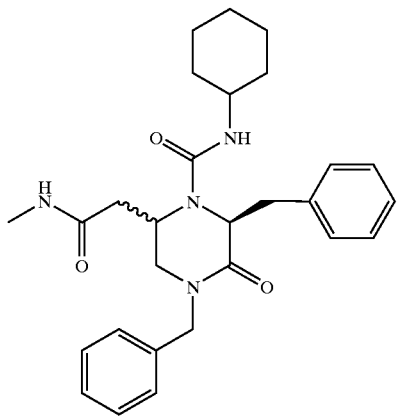

Example 6

Step 1–5

Starting from 4-bromocrotonate Merrifield Resin, the same procedure was followed as described for the preparation of Example 5.

Step 6: Cleavage of the Product

The resin was suspended in a 1:1 mixture of methylamine (40% in H$_2$O)/THF (3 mL per 100 mg of resin) and shaken for 24 h. After filtration, the resin was washed by 2×DCM (3 mL/100 mg of resin). The volatiles were removed under reduced pressure to afford crude product (69 mg). After purification on a preparative TLC plate, 35 mg of the pure desired compound were isolated as a mixture of two isomers with a 2:1 ratio (55%, based on 0.9 mmol/g loading). MS (ES) m/e (relative intensity): 477 (M+H$^+$, 70), 352 (100).

1H NMR (a mixture of two isomers, CDCl$_3$) δ7.40–7.05 (m, 10H), 5.24 (d, 1H), 5.15 (d, 1H), 4.98 (d, 1H), 4.90 (d, 1H), 4.79 (dd, 1H), 4.66 (dd, 1H), 4.58 (br, 1H), 4.35 (m, 1H), 4.22 (d, 1H), 3.77 (dd, 1H), 3.70 (d, 1H), 3.61 (m, 1H), 3.53 (dd, 1H), 3.43 (m, 1H), 3.37 (dd, 1H), 3.10 (dd, 1H), 3.02 (dd, 1H), 2.59 (d, 3H), 2.50 (d, 3H), 2.26 (d, 1H), 2.02 (d, 1H), 1.94 (d, 1H), 1.82–1.55 (m, 4H), 1.37–1.25 (m, 2H), 1.13 (m, 1H).

Example 7

Preparation of N-methyl[1-cyclohexylcarbamoyl-4-(4-methoxybenzyl)-6-(S)-methylcarbamoyl-3-oxo-piperazin-2-yl]-acetamide Reductive N-alkylation

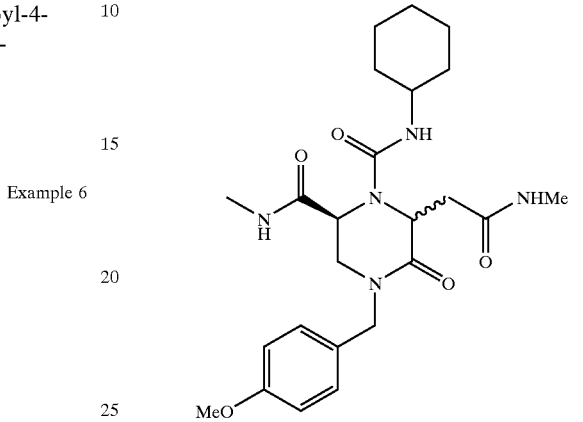

Example 7

N$^\alpha$-Boc-N$^\beta$-Fmoc-(S)-2,3-diaminopropionate Merrifield resin [Boc-(Fmoc)Dpr-Merrifield resin] (0.84 g, 0.6 mmol/g) was treated with 20% piperidine in DMF at room temperature for 30 min. The mixture was filtered and theresin was washed with DMF (3×), MeOH/DCM (5×) and DCM (3×). After drying in vacuo, the resin was mixed with anisaldehyde (0.62 mL, 10 equiv.), trimethyl orthoformate (TMOF) (3.5 mL) and DCM (3.5 mL). The resulting slurry was shaken at room temperature for 4 h. The resin was filtered, and washed with DMF (2×), MeOH/DCM (3×), and DMF (3×). The obtained resin was then mixed with 0.17 M NaBH$_3$(CN) in MeOH (7.5 mL) and 1% AcOH in DMF (7.5 mL). The suspension was shaken at room temperature overnight. The resin was filtered, washed with DMF (3×), 1 M DIEA in DCM (1×), MeOH/DCM (3×), and DCM (3×), and dried in vacuo.

Acylation

The dried resin (250 mg, 0.16 mmol) was treated with fumaric acid ethyl monoester (10 equiv.), EDC (12 equiv.) and NMP (1.7 mL). The suspension was shaken overnight. The resin was filtered, washed with DMF (3×), MeOH/DCM (5×) and DCM (3×).

De-protection and Cyclization

The above resin was treated with 20% TFA in DCM (5 mL) for 30 min, then washed with DCM (6×) and 1 M DIEA in NMP (3.5 mL). An additional portion of 1 M DIEA in NMP was added and the resulting mixture was kept at room temperature for 1 h. Filtration followed by washing [DMF (2×), DCM/MeOH (3×) and DCM (3×)] gave the cyclic product.

Urea Formation and Cleavage

The above resin was mixed with 0.5 M cyclohexyl isocyanate in DCE (3 mL) overnight. Filtration followed by washing with DMF (3×), MeOH/DCM (3×) and DCM (3×), gave the resin which was then treated with a 1:1 mixture of 40% MeNH2 aqueous solution and THF for 20 h. The resin was filtered and washed with THF. The combined filtrates were concentrated to give a residue. Purification on a preparative TLC plate (MeOH/Hexane/EtOAc: 1:3:3) gave the desired product as a mixture of two diastereoisomers. MS (ES): 474 (M+1).

Examples 8–43

The following compounds are made using the methods described and examplified above.

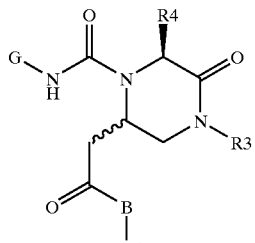

Mixture of A and B

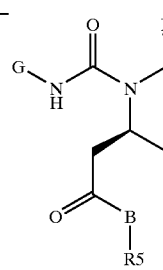 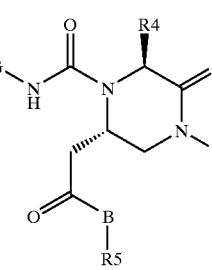

Isomer A  Isomer B

| Examples | Isomer/Mixture | R3 | R4 | G | B | R5 |
|---|---|---|---|---|---|---|
| 8 | A | 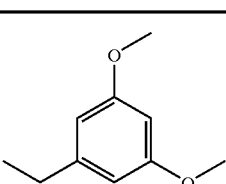 | 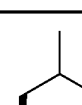 |  | NH | 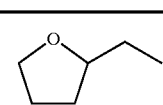 |
| 9 | B | 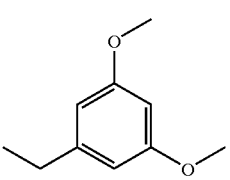 | 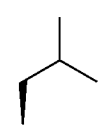 |  | NH | 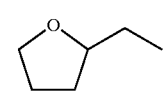 |
| 10 | A | 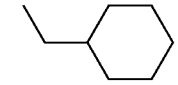 | 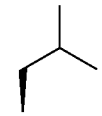 |  | NH | 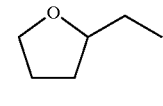 |
| 11 | B | 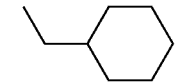 | 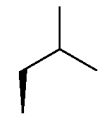 |  | NH | 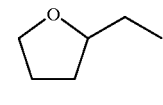 |
| 12 | A | 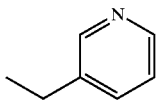 | 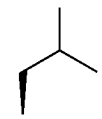 |  | NH | 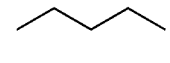 |

-continued
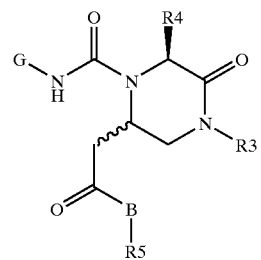
Mixture of A and B
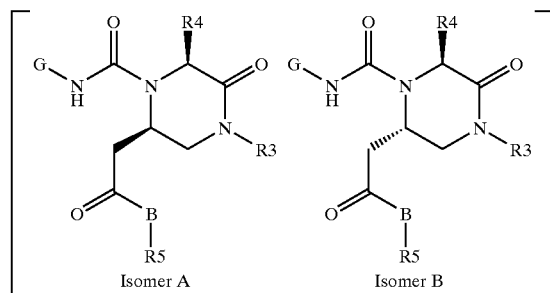
| Examples | Isomer/Mixture | R3 | R4 | G | B | R5 |
|---|---|---|---|---|---|---|
| 13 | B | 3-pyridylmethyl | isobutyl | cyclohexyl | NH | n-pentyl |
| 14 | A | 3,4-dimethoxybenzyl | isobutyl | cyclohexyl | NH | n-pentyl |
| 15 | B | 3,4-dimethoxybenzyl | isobutyl | cyclohexyl | NH | n-pentyl |
| 16 | M | 3,5-dimethoxybenzyl | isobutyl | cyclohexyl | O | H |
| 17 | A | 3,5-dimethoxybenzyl | isobutyl | cyclohexyl | O | H |
| 18 | B | 3,5-dimethoxybenzyl | isobutyl | cyclohexyl | O | H |

-continued

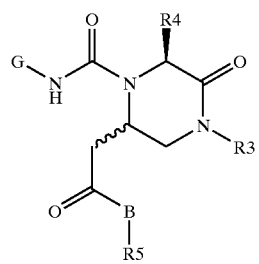
Mixture of A and B

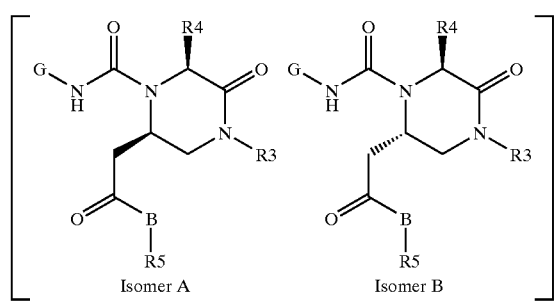
Isomer A    Isomer B

| Examples | Isomer/Mixture | R3 | R4 | G | B | R5 |
|---|---|---|---|---|---|---|
| 19 | A | 3,5-dimethoxyphenyl | isobutyl | piperidin-1-yl | NH | Me |
| 20 | B | 3,5-dimethoxyphenyl | isobutyl | piperidin-1-yl | NH | Me |
| 21 | A | 3,4-dimethoxyphenyl | isobutyl | cyclohexyl | NH | tetrahydrofuran-2-yl |
| 22 | B | 3,4-dimethoxyphenyl | isobutyl | cyclohexyl | NH | tetrahydrofuran-2-yl |
| 23 | A | 4-(dimethylamino)phenyl | isobutyl | cyclohexyl | NH | tetrahydrofuran-2-yl |
| 24 | B | 4-(dimethylamino)phenyl | isobutyl | cyclohexyl | NH | tetrahydrofuran-2-yl |

-continued
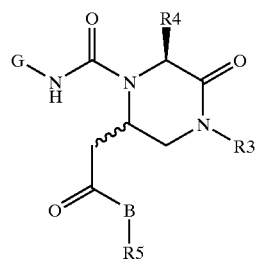
Mixture of A and B
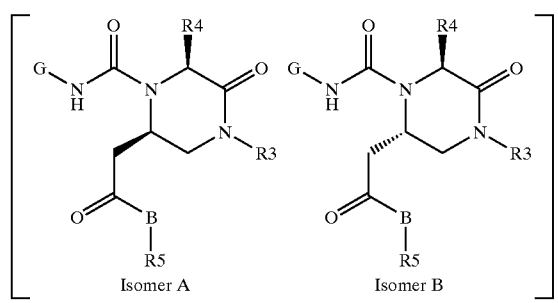
Isomer A      Isomer B
| Examples | Isomer/Mixture | R3 | R4 | G | B | R5 |
|---|---|---|---|---|---|---|
| 25 | M | 3,5-dimethoxyphenyl with ethyl | isobutyl | cyclohexyl | O | Me |
| 26 | A | 3,5-dimethoxyphenyl with ethyl | isobutyl | cyclohexylmethyl | NH | Me |
| 27 | B | 3,5-dimethoxyphenyl with ethyl | isobutyl | cyclohexylmethyl | NH | Me |
| 28 | A | hexadienyl | isobutyl | cyclohexyl | NH | Me |
| 29 | B | phenylethyl | isobutyl | cyclohexyl | NH | Me |

-continued
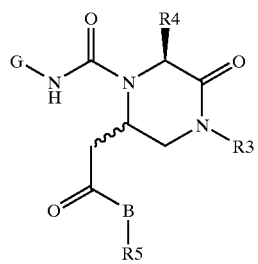
Mixture of A and B
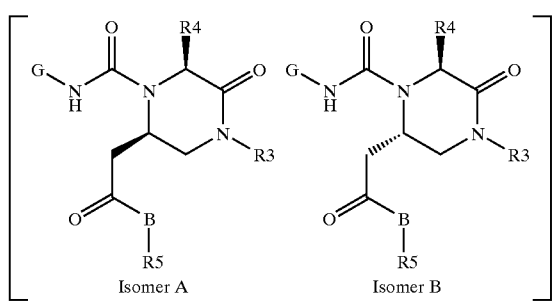
| Examples | Isomer/Mixture | R3 | R4 | G | B | R5 |
|---|---|---|---|---|---|---|
| 30 | A | 3,5-dimethoxy-ethylphenyl | isobutyl | cyclopentyl | NH | Me |
| 31 | B | 3,5-dimethoxy-ethylphenyl | isobutyl | cyclopentyl | NH | Me |
| 32 | M | 3,5-dimethoxy-ethylphenyl | isobutyl | cyclohexyl | NH | Me |
| 33 | A | 3,5-dimethoxy-ethylphenyl | isobutyl | cyclohexyl | NH | Me |
| 34 | B | 3,5-dimethoxy-ethylphenyl | isobutyl | cyclohexyl | NH | Me |

-continued

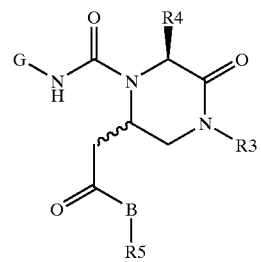

Mixture of A and B

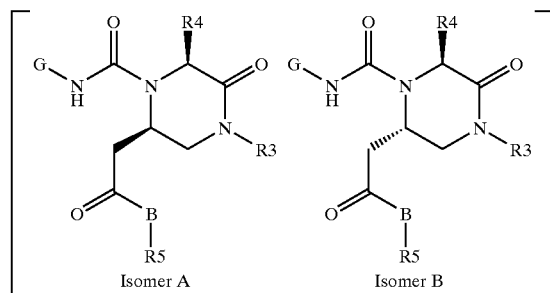

| Examples | Isomer/Mixture | R3 | R4 | G | B | R5 |
|---|---|---|---|---|---|---|
| 35 | M | 3,5-dimethoxyphenylethyl | isobutyl | cyclohexyl | NH | n-pentyl |
| 36 | A | 3,5-dimethoxyphenylethyl | isobutyl | cyclohexyl | NH | n-pentyl |
| 37 | B | 3,5-dimethoxyphenylethyl | isobutyl | cyclohexyl | NH | n-pentyl |
| 38 | A | cyclohexylethyl | isobutyl | cyclohexyl | NH | n-pentyl |
| 39 | B | cyclohexylethyl | isobutyl | cyclohexyl | NH | n-pentyl |
| 40 | M | cyclohexylethyl | isobutyl | cyclohexyl | NH | Me |

-continued

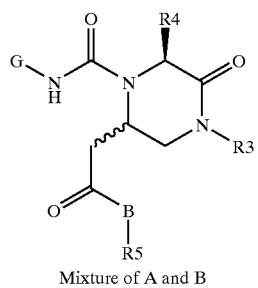

Mixture of A and B

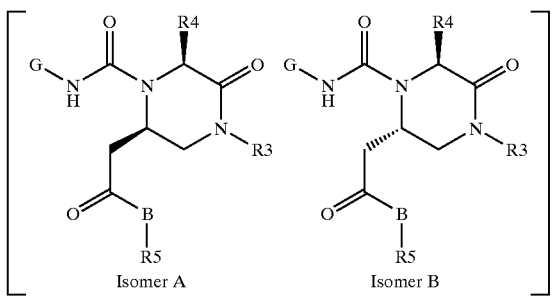

[Isomer A    Isomer B]

| Examples | Isomer/Mixture | R3 | R4 | G | B | R5 |
|---|---|---|---|---|---|---|
| 41 | M | 3,5-dimethoxyphenethyl | n-butyl | cyclohexyl | NH | Me |
| 42 | M | 3,5-dimethoxyphenethyl | isobutyl | cyclohexyl | NH | isopropyl |
| 43 | M | 3,5-dimethoxyphenethyl | isobutyl | cyclohexyl | NH | HOCH2CH2CH2 |

Example 8

$^1$H NMR (CDCl$_3$): δ0.96 (d, J=6.6 Hz 6H), d 1.08–1.70 (m, 8H), d 1.78–2.06 (m, 7H), d 2.22–2.30 (m, 1H), d 2.56–2.65 (m, 1H), d 3.04–3.13 (m, 2H), d 3.46–3.57 (m, 3H), d 3.70–3.95 (m, 3H), d 3.75 (s, 6H), d 4.35 (dd, J=14.7, 5.7 Hz, 1H), d 4.45–4.50 (m, 1H), d 4.62 (dd, J=14.4, 5.1 Hz, 1H), d 4.83 (t, J=6.6 Hz, 1H), d 5.74 (br, 1H), d 6.13 (br, 1H), d 6.36 (s, 3H).

Example 9

$^1$H NMR (CDCl$_3$): d 0.89 (d, J=6.3 Hz, 3H), d 1.06 (d, J=6.3 Hz, 3H), d 1.07–1.17 (q, J=12.0 Hz, 2H), d 1.25–1.69 (m, 7H), d 2.30 (d, J=14.1 Hz, 1H), d 2.94–3.12 (m, 1H), d 3.23 (d, J=13.8 Hz, 1H), d 3.30–3.48 (m, 1H), d 3.57–3.64 (m, 2H), d 3.68–3.90 (m, 3H), d 3.74 (s, 6H), d 4.14 (br d, J=7.2 Hz, 1H), d 4.38 (br dd, J=10.8, 3.6 Hz, 1H), d 4.52 (s, 2H), d 5.05 (br dd, J=13.2, 10.5 Hz, 1H), d 5.76 (br d, J=5.7 Hz, 1H), d 6.37–6.41 (m, 3H).

Example 10

$^1$H NMR (CDCl$_3$): δ0.90–0.97 (m, 9H), δ1.15–2.06 (m, 23H), δ2.40 (dd, J=14.7, 4.8 Hz 1H), δ2.66 (dq, J=15.3, 4.5 Hz, 1H), δ3.07–3.30 (m, 4H), δ3.52–3.64 (m, 3H), δ6 3.73–3.97 (m, 5H), δ4.50 (t, J=6.0 Hz, 1H), δ4.62 (t, J=7.2 Hz, 1H), δ5.47 (t, J=7.2 Hz, 1H), δ6.22 (br, 1H).

Example 11

$^1$H NMR (CDCl$_3$): δ0.89 (d, J=6.6 Hz, 3H), d 1.05 (d, J=6.6 Hz, 3H), d 0.87–2.03 (m, 28H), d 2.28 (dd, J=14.1, 9.3 Hz, 1H), d 2.48 (d, J=13.5 Hz, 1H), d 2.74 (dd, J=13.8, 6.0 Hz, 1H), d 3.07–3.21 (m, 1H), d 3.43–3.95 (m, 8H), d 4.14 (t, J=6.3 Hz, 1H), d 4.30 (br d, J=7.2 Hz, 1H), d 4.63 (br t, J=9.0 Hz, 1H), d 6.29 (br, 1H).

Example 12

$^1$H NMR (CDCl$_3$): δ 0.89–0.98 (m, 9H), d 1.10–1.91 (m, 17H), d 2.20 (dd, J=15.3, 5.1 Hz, 1H), d 2.58 (dd, J=15.3, 8.7 Hz, 1H), d 3.08–3.24 (m, 3H), d 3.53–3.62 (m, 2H), d 4.34 (d, J=14.7 Hz, 1H), d 4.52–4.57 (m, 1H), d 4.78–4.83 (m, 2H), d 5.76 (br d, J=6.3 Hz, 1H), d 6.07 (br, 1H), d 7.25–7.29 (m, 1H), d 7.60–7.63 (m, 1H), d 8.50–8.54 (m, 2H).

Example 13

$^1$H NMR (CDCl$_3$): d 0.90–0.94 (m, 6H), d 1.06–2.00 (m, 21H), d 2.36 (d, J=12.9 Hz, 1H), d 3.11–3.19 (m, 2H), d 3.43 (dd, J=13.5, 2.1 Hz, 1H), d 3.61–3.66 (m, 2H), d 4.21–4.29 (m, 2H), d 4.55 (d, J=14.7 Hz, 1H), d 4.73–4.80 (m, 2H), d 5.63 (br, 1H), d 7.29–7.30 (m, 1H), d 7.6–7.71 (m, 1H), d 8.57–8.58 (m, 2H).

Example 14

$^1$H NMR (CDCl$_3$): d 0.88–0.99 (m, 9H), d 1.10–1.19 (m, 3H), d 1.29–1.48 (m, 7H), d 1.55–1.67 (m, 6H), d 1.80–1.95 (m, 4H), d 1.21 (dd, J=15.0, 5.7 Hz, 1H), d 2.53 (dd, J=15.0, 8.1 Hz, 1H), d 3.10–3.29) m, 3H), d 3.48–3.54 (m, 2H), d 3.86 (s, 6H), d 4.35 (d, J=14.1 Hz, 1H), d 4.48 (br, 1H), d 4.63–4.70 (m, 2H), d 5.51 (br, 1H), d 5.80 (br, 1H), d 6.79 (s, 3H).

Example 15

$^1$H NMR (CDCl$_3$): δ 0.87–0.98 (m, 6H), d 1.08 (d, J=6.3 Hz, 3H), d 1.06–1.19 (m, 3H), d 1.24–1.42 (m, 6H), d 1.48–1.68 (m, 5H), d 1.88–1.96 (m, 4H), d 2.25 (d, J=14.1 Hz, 1H), d 3.04–3.14 (m, 2H), d 3.27 (d, J=13.2 Hz, 1H), d 3.60 (br d, J=12.9 Hz, 2H), d 3.85 (s, 6H), d 4.10 (br d, J=8.4 Hz, 1H), d 4.34–4.39 (m, 2H), d 4.68 (br d, J=9.9 Hz, 1H), 4.93 (br, 1H), d 5.28 (br, 1H), d 6.69–6.87 (m, 3H).

Example 16

1H NMR (CDCl13): d 1.03–1.80 (m, 7H), d 1.11 (t, J=6.3 Hz, 6H), d 1.96–2.07 (m, 4H), d 2.42 (dd, J=15.9, 6.3 Hz, 1H), d 2.82 (dd, J=15.9, 6.9 Hz, 1H), d 3.26 (dd, J=13.2, 5.7 Hz, 1H), d 3.55–3.86 (m, 5H), d 3.88 (s, 6H), d 4.45 (d, J=14.4 Hz, 1H), d 4.57 (t, J=6.6 Hz, 1H), d 4.69 (t, J=6.0 Hz, 1H), d 4.80 (d, J=14.4 Hz, 1H), d 5.09 (br d, J=5.7 Hz, 1H), d 6.48 (s, 3H).

Example 17

1H NMR (CDCl3): d 1.04 (d, J=6.6 Hz, 3H), d 1.19 (d, J=6.3 Hz, 3H), d 1.18–1.28 (m, 5H), d 1.67–1.80 (m, 5H), d 1.99–2.08 (m, 3H), d 2.42 (dd, J=15.6, 8.7 Hz, 1H), d 2.59 (dd, J=15.6, 3.3 Hz, 1H), d 3.47 (d, J=13.5 Hz, 1H), d 3.71 (dd, J=14.1, 3.6 Hz, 1H), d 3.86 (s, 6H), d 4.23 (d, J=14.7 Hz, 1H), d 4.31 (dd, J=9.9, 4.8 Hz, 1H), d 4.49 (br, 1H), d 4.63 (br d, J=7.2 Hz, 1H), d 5.06 (d, J=14.4 Hz, 1H), d 6.60–6.40 (br, 1H), d 6.48 (s, 3H).

Example 18

1H NMR (CDCl3): d 1.09 (t, J=6.3 Hz, 6H), d 1.22 (d, J=6.9 Hz, 1H), d 1.60–2.21 (m, 8H), d 2.30 (s, 1H), d 2.34–2.37 (m, 2H), d 2.78 (t, J=5.7 Hz, 1H), d 2.91 (d, J=4.8 Hz, 3H), d 3.15–3.21 (m, 2H), d 3.40–3.50 (m, 1H), d 3.66 (dd, 9.9,3.3 Hz, 1H), d 3.89 (s, 6H), d 4.47 (d, J=14.4 Hz, 1H), d 4.77 (d, J=14.7 Hz, 1H), d 6.50 (s, 3H), d 6.70 (br, 1H).

Example 19

1H NMR (CDCl3): d 1.04 (d, J=6.3 Hz, 3H), d 1.21 (d, J=6.0 Hz, 3H), d 1.62–2.37 (m, 6H), d 2.77 (d, J=4.8 Hz, 3H), d 2.92 (d, J=4.5 Hz, 3H), d 3.30 (d, J=13.5 Hz, 1H), d 3.81 (d, J=12.9 Hz, 1H), d 3.87 (s, 6H), d 4.21 (br d, J=7.5 Hz, 1H), d 4.32 (d, J=14.4 Hz, 1H), 4.60 (br d, J=7.5 Hz, 1H), d 4.96 (d, J=13.8 Hz, 1H), d 5.31 (br, 2H), d 6.54 (s, 1H), d 6.60 (s, 2H).

Example 20

$^1$H NMR (CDCl$_3$): d 0.96 (d, J=6.3 Hz, 6H), d 1.06–1.21 (m, 3H), d 1.26–1.39 (m, 3H), d 1.44–1.66 (m, 4H), d 1.70, 1.98 (m, 8H), d 2.22 (dt, J=15.3, 4.8 Hz, 1H), d 2.57 (dq, J=15.3, 4.2 Hz, 1H), d 3.00–3.13 (m, 2H), d 3.46–3.57 (m, 3H), d 3.70–3.90 (m, 2H), d 3.85 (s, 6H), d 4.36 (dd, J=14.4, 4.8 Hz, 1H), d 4.44–4.49 (m, 1H), d 4.62 (dd, J=14.4, 4.2 Hz, 1H), d 4.80 (t, J=6.9 Hz, 1H), d 5.70 (br t, J=6.9 Hz, 1H), d 6.09 (br, 1H), d 6.75–6.81 (m, 3H).

Example 21

$^1$H NMR (CDCl$_3$): d 0.90 (d, J=6.6 Hz, 3H), d 1.08 (d, J=6.6 Hz, 3H), d 1.06–1.19 (m, 3H), d 1.22–1.38 (m, 2H), d 1.42–1.71 (m, 6H), d 1.78–1.98 (m, 7H), d 2.28 (d, J=14.1 Hz, 1H), d 2.94–3.06 (m, 1H), d 3.31 (d, J=12.9 Hz, 1H), d 3.38–3.48 (m, 1H), d 3.61 (d, J=10.5 Hz, 2H), d 3.70–3.92 (m, 3H), d 3.85 (d, J=6.2 Hz, 6H), d 4.13 (d, J=9.9 Hz, 1H), d 4.37 (dd, J=11.1, 4.2 Hz, 1H), d 4.48 (dd, J=14.1, 9.3 Hz, 1H), d 4.59 (dd, J=14.1, 6.9 Hz, 1H), d 4.99 (br t, J=9.0 Hz, 1H), d 5.68 (br, 1H), d 6.83 (s, 2H), d 6.88 (s, 1H).

Example 22

1H NMR (CDCl3): d 0.92–0.96 (m, 6H), d 1.07–1.25 (m, 3H), d 1.32–1.40 (m, 3H), d 1.45–1.70 (m, 5H), d 1.85–1.99 (m, 6H), d 2.19 (dd, J=16.1, 5.4 Hz, 1H), d 2.50–2.56 (m, 1H), d 2.95 (s, 6H), d 3.03–3.10 (m, 2H), d 3.44–3.60 (m, 3H), d 3.69–3.75 (m, 1H), d 3.79–3.88 (m, 2H), d 4.23 (d, J=14.1 Hz, 1H), d 4.44–4.49 (m, 1H), d 4.70 (d, J=14.4 Hz, 1H), d 4.78 (t, J=6.6 Hz, 1H), d 5.65 (br t, J=7.5 Hz, 1H), d 6.01 (br, 1H), d 6.66 (d, J=8.7 Hz, 2H), d 7.11 (d, J=8.7 Hz, 2H).

Example 23

$^1$H NMR (CDCl$_3$): d 0.91 (d, J=6.6 Hz, 3H), d 0.98 (d, J=6.6 Hz, 3H), d 0.99–1.21 (m, 2H), d 1.23–1.71 (m, 8H), d 1.78–1.96 (m, 7H), d 2.20 (d, J=14.7 Hz, 1H), d 2.84–3.10 (m, 1H), d 2.95 (s, 6H), d 3.18 (dd, J=12.3, 5.7 Hz, 1H), d 3.28–3.44 (m, 1H), d 3.62 (d, J=10.5 Hz, 2H), d 3.67–3.88 (m, 1H), d 4.05 (br d, J=4.8 Hz, 1H), d 4.11 (t, J=13.8 Hz, 1H), d 4.43 (br dd, 1H), d 4.87 (t, J=13.2 Hz, 1H), d 5.17 (br t, J=6.6 Hz, 1H), d 5.38 (br, 1H), d 6.69 (d, J=8.7 Hz, 2H), d 7.20 (d, J=6.6 Hz, 2H).

Example 24

1H NMR (CDCl3): d 1.03–2.06 (m, 28H), d 2.36 (dd, J=16.5,9.9 Hz, 2H), d 2.44 (dd, J=15.0, 5.7 Hz, 1H), d 2.66 (d, J=14.4 Hz, 2H), d 2.95 (dd, J=16.5,7.8 Hz, 1H), d 3.22 (dd, J=12.9, 4.2 Hz, 1H), d 3.49 (d, J=13.8 Hz, 2H), d 3.61–3.81 (m, 10H), d 3.88 (s, 12H), d 4.31–4.46 (m, 8H), d 4.56–4.68 (m, 6H), d 4.86–4.90 (m, 2H), d 5.22 (br d, J=7.5 Hz, 1H), d 6.44–6.51 (m, 6H).

Example 25

$^1$H NMR (CD$_3$OD): d 1.08 (t, J=6.6 Hz, 6H), d 1.34–1.41 ((m, 4H), d 1.62–1.93 (m, 9H), d 2.50 (dd, J=15.3, 6.0 Hz, 1H), d 2.78 (dd, J=12.0, 8.1 Hz, 1H), d 2.81 (s, 3H), d 3.12 (t, J=6.2 Hz, 2H), d 3.39 (dd, J=13.2, 4.8 Hz, 1H), d 3.43 (s, 1H), d 3.68 (d, J=13.2, 6.0 Hz, 1H), d 3.88 (s, 6H), d 4.03

(m, 1H), d 4.51 (d, J=14.7 Hz, 1H), d 4.58 (m, 1H), d 4.77 (d, J=14.7 Hz, 1H), d 5.10 (dd, J=9.0, 4.8 Hz, 1H), d 6.54 (d, J=2.2 Hz, 2H), d 7.02 (d, J=2.2 Hz, 1H).

Example 26

$^1$H NMR (CD$_3$OD): d 0.98–1.10 (m, 2H), d 1.02 (d, J=6.3 Hz, 3H), d 1.15 (d, J=6.3 Hz, 3H), d 1.24–1.39 (m, 2H), d 1.50–1.65 (m, 1H), d 1.71–1.86 (m, 7H), d 2.31 (dd, J=15.3, 9.0 Hz, 1H), d 2.48 (dd, J=15.0, 3.1 Hz, 1H), d 2.78 (s, 3H), d 3.03–3.21 (m, 2H), d 3.52 (dd, J=13.8, 1.8 Hz, 1H), d 3.85 (dd, J=13.5, 2.4 Hz, 1H), d 3.88 (s, 6H), d 4.39 (br d, J=14.1 Hz, 2H), d 4.62 (q, J=4.8 Hz, 1H), d 4.91 (d, J=14.4 Hz, 1H), d 6.53–6.57 (m, 3H).

Example 27

1H NMR (CDCl3): d 1.10 (t, J=6.6 Hz, 6H), d 1.22–1.53 (m, 6H), d 1.68–2.01 (m, 7H), d 2.32 (dd, J=15.0, 6.0 Hz, 1H), d 2.68 (dt, J=15.0, 7.5 Hz, 1H), d 2.87 (d, J=4.8 Hz, 3H), d 3.23 (dd, J=12.6, 4.2 Hz, 1H), d 3.64 (dd, J=12.9, 5.1 Hz, 1H), d 3.64–3.77 (m, 1H), d 4.46 (d, J=14.2 Hz, 1H), d 4.61 (m, 1H), d 4.85 (dd, J=7.5, 6.6 Hz, 1H), d 4.93 (d, J=14.7 Hz, 1H), d 5.62 (br, d, J=7.8 Hz, 1H), d 5.92 (br, 1H), d 7.35–7.50 (m, 5H).

Example 28

1H NMR (CDCl3): d 1.04 (t, J=6.6 Hz, 3H), d 1.20 (t, J=6.6 Hz, 3H), d 1.23–1.32 (m, 3H), d 1.37–1.47 (m, 4H), d 1.66–1.81 (m, 4H), d 1.93–1.99 (m, 4H), d 2.34 (d, J=14.4 Hz, 1H), d 2.72 (d, J=4.8 Hz, 3H), d 3.32 (d, J=13.8 Hz, 1H), d 3.73–3.79 (m, 2H), d 4.21 (br d, J=8.1 Hz, 1H), d 4.44 (d, J=14.1 Hz, 1H0, d 4.52 (dd, 10.5, 4.2 Hz, 1H), d 5.04 (br d, J=13.8 Hz, 3H), d 7.45–7.50 (m, 5H).

Example 29

$^1$H NMR (CDCl$_3$): d 1.10 (t, J=6.3 Hz, 6H), d 1.44–1.57 (m, 3H), d 1.66–2.08 (m, 8H), d 2.37 (dd, J=15.0, 5.7 Hz, 1H), d 2.69 (dd, J=15.0, 7.8 Hz, 1H), d 2.89 (d, J=4.5 Hz, 3H), d 3.25 (dd, J=12.9, 5.1 Hz, 1H), d 3.63 (dd, J=12.9, 5.4 Hz, 1H), d 3.89 (s, 6H), d 4.11–4.18 (m, 1H), d 4.41 (d, J=14.1 Hz, 1H), d 4.60 (dd, J=7.5, 2.1 Hz, 1H), d 4.84 (d, J=14.1 Hz, 1H), d 4.87 (d, J=13.8 Hz, 1H), d 5.76 (br d, J=6.3 Hz, 1H), d 5.94 (br d, J=4.2 Hz, 1H), d 6.50 (s, 3H).

Example 30

$^1$H NMR (CDCl$_3$): d 1.04 (d, J=6.6 Hz, 3H), d 1.20 (d, J=6.3 Hz, 3H), d 1.44–1.5 (m, 2H), d 1.62–1.83 (m, 6H), d 1.91–2.16 (m, 4H), d 2.35 (d, J=14.1 Hz, 1H), d 2.78 (d, J=5.1 Hz, 3H), d 3.33 (dd, J=13.5, 1.5 Hz, 1H), d 3.78 (dd, J=13.8, 1.8 Hz, 1H), d 3.89 (s, 6H), d 4.20 (dd, J=13.5, 6.9 Hz, 2H), d 4.40 (d, J=14.4 Hz, 1H), d 4.53 (dd, J=10.2, 3.9 Hz, 1H), d 4.90 (d, J=14.1 Hz, 1H), d 5.18 (br d, J=6.3 Hz, 1H), d 5.39 (br, 1H), d 6.53 (t, J=2.1 Hz, 1H), d 6.59 (d, J=2.7 Hz, 2H).

Example 38

1H NMR (CDCl3): d 0.89–0.99 (m, 12H), d 1.05–1.93 (m, 26H), d 2.39 (dd, J=14.7, 6.0 Hz, 1H), d 2.67 (dd, J=15.0, 7.2 Hz, 1H), d 3.11–3.33 (m, 4H), d 3.61 (dd, J=12.9, 5.1 Hz, 2H), d 4.51 (t, J=6.3 Hz, 2H), d 2.36 (br, d, J=6.0 Hz, 1H), d 6.01 (br, 1H).

Biological Results

A reporter gene assay utilizing transfected human hepatoma (HepG2) cells is used to screen for compounds that transcriptionally activate a PPRE via a PPAR-gamma mediated pathway. Cells are exposed to experimental compounds dissolved in DMSO for 36–48 h prior to determination of reporter gene activity. 15dPGJ2 (2 μM) is used as positive control and vehicle (DMSO) is used as a negative control. The data is expressed in Table 1 below as μM to achieve EC50.

TABLE 1

| EXAMPLES | EC5O (μM) |
| --- | --- |
| 39 | 1.35 |
| 32 | 0.62 |
| 41 | 2.35 |
| 16 | 3.6 |
| 25 | >10 |
| 42 | 0.25 |
| 43 | >1 |
| 35 | 0.12 |

Animal Tests

Compounds prepare in accordance with Examples 8 and 36 were evaluated for their effect on serum glucose and serum insulin in db/db mice (C578BL/KsJ-db/db Jcl). The compounds were dissolved in a vehicle consisting of 2% Tween80 in distilled water and administered orally. Dosage volume was 10 ml/kg body weight. All aspects of the work including experimentation and disposal of the animals was performed in general accordance with the International Guiding Principles for Biomedical Research Involving Animals (CIOMS Publication No. ISBN 92 90360194, 1985). Glucose-HA Assay kits (Wako, Japan) were used for determination of serum glucose and ELISA Mouse Insulin Assay kits (SPI bio, France) were utilized for determination of insulin. The positive control was troglitazone (Helios Pharmaceutical, Louisville, Ky.).

The animals were divided into twenty groups of four animals each. The animals weighed 52±5 gms at age 8–10 weeks. During the experiment the animals were provided free access to laboratory chow (Fwusow Industry Co., Taiwan) and water Prior to any treatment a blood sample (pretreatment blood) was taken from each animal. Four groups of animals, the vehicle groups, received only doses of the vehicle. Each of the vehicle groups received of 100, 30, 10 or 1 ml/kg body weight of the vehicle orally. A triglitazone solution (10 ml/kg body weight in tween 80/water) was administered orally to the four positive control groups in doses of 100, 30, 10 and 1 ml/kg body weight respectively. The compound of Example 8 was administered orally as a solution (10 ml/kg body weight in tween 80/water) to four groups of animals with each group receiving a different dose of the compound. The dosage rates were 100, 30, 10 and 1 ml/kg body weight with only one dosage rate administered to each group. The compound of Example 36 was likewise solubilized (10 ml/kg body weight in tween 80/water) and administered to four groups of animals in doses of 100, 30, 10 and 1 ml/kg body weight with each group receiving a different dose. The vehicle, positive control and test compound solutions were administered to the groups immediately, 24 hours and 48 hours after drawing the pretreatment blood. Blood was withdrawn (post treatment blood) 1.5 hours after administration of the last dose.

The serum glucose levels of the blood samples was determined enzymatically (Mutaratose-GOD) and the insulin levels by ELISA (mouse insulin assay kit). The mean±SEM of each group was calculated and the percent inhibition of serum glucose and insulin was obtained by comparison between pretreatment blood and post treatment blood. The percentage of reduction of the serum glucose and insulin levels in the post treatment blood relative to the pretreatment blood was determined and the Unpaired students t test was applied for the comparison between the control and test solution groups and the vehicle group. A significant difference was considered at P<0.05.

The positive control, troglitazone, showed a significant reduction of glucose level at 10 mg/kg body weight (25±2%). Test solutions containing the compound of Example 8 exhibited a significant reduction of serum glucose at a dosage rate of 100 mg/kg body weight (P<0.01) relative to the vehicle treated groups. Test solutions containing the compound of Example 36 exhibited a significant reduction of serum glucose at dosage rates of 30 mg/kg body weight (P<0.05) and 100 mg/kg body weight (P<0.01) relative to the vehicle treated groups. The results of the animal tests are setforth in Table 2 below.

TABLE 2

| Dose (mg/kg) | Serum Glucose (% reduction) | Serum Insulin (% reduction) |
|---|---|---|
| EXAMPLE 8 | | |
| 100 | 41 ± 6 | 6 ± 2.5 |
| 30 | 14 ± 2 | 5 ± 4 |
| 10 | 18 ± 6 | 1 ± 4 |
| 3 | −1 ± 3 | −7 ± 3 |
| 1 | 9 ± 8 | 3 ± 7 |
| EXAMPLE 36 | | |
| 100 | 40 ± 7 | 2 ± 4 |
| 30 | 37 ± 8 | 1 ± 2 |
| 10 | −4 ± 7 | −9 ± 6 |
| 3 | 0 ± 2 | −9 ± 2 |
| 1 | −1 ± 2 | 8 ± 7 |

The PPAR-gamma agonist compounds of the present invention are useful in treatment conditions where modification of the effects of PPAR-gamma is of therapeutic benefit in treatment methods for mammals, including humans, involving the administration of therapeutically effective amounts of a compound of Formula 1 or a pharmaceutically acceptable salt or solvate thereof. The PPAR-gamma agonist activity of the compounds of the present invention make them particularly useful as medicaments in the treatment of PPAR-gamma mediated diseases. For example, diseases such as diabetes, both Type I and Type II, hyperglycemia, insulin resistance, obesity and certain vascular and cardiovascular diseases such as artherosclerosis and hypertension are associated with increased PPAR-gamma levels. It will be understood that the term treatment refers also to the use of the compounds of Formula 1 for the prophylaxis or prevention of PPAR-gamma mediated diseases.

The compounds of Formula 1 are provided in suitable topical, oral and parenteral pharmaceutical formulations for use in the treatment of PPAR-gamma mediated diseases. The compounds of the present invention may be administered orally as tablets or capsules, as oily or aqueous suspensions, lozenges, troches, powders, granules, emulsions, syrups or elixars. The compositions for oral use may include one or more agents for flavoring, sweetening, coloring and preserving in order to produce pharmaceutically elegant and palatable preparations. Tablets may contain pharmaceutically acceptable excipients as an aid in the manufacture of such tablets. As is conventional in the art these tablets may be coated with a pharmaceutically acceptable enteric coating, such as glyceryl monostearate or glyceryl distearate, to delay disintegration and absorption in the gastrointestinal tract to provide a sustained action over a longer period.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients may be a suspending agent, such as sodium carboxymethyl cellulose, methyl cellulose, hydroxypropylmethyl cellulose, sodium alginate, polyvinylpyrrolidone, gum tragacanth and gum acacia; a dispersing or wetting agent that may be a naturally occuring phosphatide such as lecithin, a condensation product of ethylene oxide and a long chain fatty acid, for example polyoxyethylene stearate, a condensation product of ethylene oxide and a long chain aliphatic alcohol such as heptadecaethylenoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pharmaceutical compositions may be in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic perenterally-acceptable diluent or solvent, for example as a solution in 1,3-butanediol. Among the accetable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

The compounds may also be administered in the form of suppositories for rectal administration of the drug. These compositions can be prepared by mixing the drug with a suitable non-irritating excipient that is solid at about room temperature but liquid at rectal temperature and will therefor melt in the rectum to release the drug. Such materials include cocoa butter and other glycerides.

For topical use preparations, for example, creams, ointments, jellies solutions, or suspensions, containing the compounds of the present invention are employed.

The compounds of the present invention may also be administered in the form of liposome delivery systems such as small unilamellar vesicles, large unilamellar vesicles and multimellar vesicles. Liposomes can be formed from a variety of phospholipides, such as cholesterol, stearylamine or phosphatidylcholines.

Dosage levels of the compounds of the present invention are of the order of about 0.5 mg/kg body weight to about 100 mg/kg body weight. A preferred dosage rate is between about 30 mg/kg body weight to about 100 mg/kg body weight. It will be understood, however, that the specific dose level for any particular patient will depend upon a number of factors including the activity of the particular compound being administered, the age, body weight, general health, sex, diet, time of administration, route of administration, rate of excretion, drug combination and the severity of the particular disease undergoing therapy. To enhance the therapeutic activity of the present compounds they may be administered concomitantly with other orally active antidiabetic compounds such as the sulfonylureas, for example, tolbutamide and the like.

As will be understood by those skilled in the art, various arrangements which lie within the spirit and scope of the invention other than those described in detail in the specification will occur to those persons skilled in the art. It is therefor to be understood that the invention is to be limited only by the claims appended hereto.

What is claimed is:

1. A compound having the structure according to Formula (I) and pharmaceutically acceptable salts thereof, wherein the broken line represents an optional double bond;

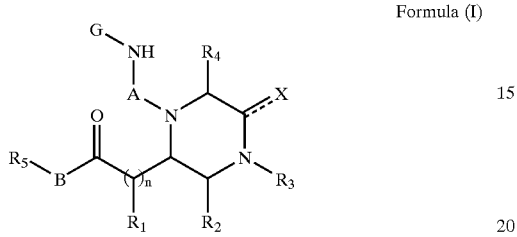

Formula (I)

Wherein

X is H, O, S;

A is —C(O)—, —S(O)m—;

B is O, S, $NR_6$, wherein $R_6$ is H, $C_1$–$C_6$ alkyl, $C_2$–$C_6$ alkenyl and $C_2$–$C_6$ alkynyl and $C_3$–$C_6$ cycloalkyl;

n is 0 or 1;

m is 1 or 2;

G is $C_3$–$C_{10}$ cycloalkyl, $C_4$–$C_{10}$ cycloalkenyl, saturated $C_3$–$C_{10}$ heterocyclyl, $C_3$–$C_{10}$ cycloalkyl-$C_1$–$C_3$ alkyl, $C_4$–$C_{10}$ cycloalkenyl-$C_1$–$C_3$ alkyl, saturated $C_3$–$C_{10}$ heterocyclyl-$C_1$–$C_3$ alkyl, said cycloalkyl, cycloalkenyl, heterocyclyl and alkyl optionally substituted with 1 to 3 groups of $R_s$, wherein heterocyclyl contains 1 to 4 heteroatoms which may be nitrogen, sulfur or oxygen atom;

$R_1$ is hydrogen, hydroxy, thio, nitro, cyano, azido, amino, trifluoromethyl, trifluoromethoxy, $C_1$–$C_6$ alkyl, $C_1$–$C_6$ alkyloxy, $C_1$–$C_6$ alkylthio, $C_1$–$C_6$ alkylamino, $C_1$–$C_6$ alkenyl, $C_1$–$C_6$ alkenyloxy, $C_1$–$C_6$ alkenylamino, $C_3$–$C_8$ cycloalkyl, $C_3$–$C_8$ cycloalkyloxy, $C_3$–$C_8$ cycloalkylamino, $C_3$–$C_8$ cycloalkylthio, $C_1$–$C_6$ alkylcarbonylamino, $C_3$–$C_8$ cycloalkylcarbonylamino, $C_5$–$C_{10}$ aryl, $C_5$–$C_{10}$ heteroaryl or $C_5$–$C_{10}$ saturated heteroaryl; said aryl, heteroaryl, alkyl, alkenyl, and cycloalkyl optionally substituted with 1 to 3 groups of $R_s$;

$R_2$, $R_3$, and $R_5$ independently are H, trifluoromethyl, $C_5$–$C_{10}$ aryl, $C_5$–$C_{10}$ heteroaryl, $C_1$–$C_{10}$ alkyl, $C_2$–$C_{10}$ alkenyl, $C_2$–$C_{10}$ alkynyl, $C_3$–$C_{10}$ cycloalkyl, saturated $C_5$–$C_{10}$ heteroaryl, $C_5$–$C_{10}$ aryl-$C_1$–$C_{10}$ alkyl, $C_5$–$C_{10}$ heteroaryl-$C_1$–$C_{10}$ alkyl, $COR_7$, $CO_2R_7$, $CONR_7R_8$, $SO_2NR_7R_8$, said aryl, heteroaryl, alkyl, alkenyl, and cycloalkyl optionally substituted with 1 to 3 groups of $R_s$;

$R_4$ is selected from the group consisting of trifluoromethyl, $C_5$–$C_{10}$ aryl, $C_5$–$C_{10}$ heteroaryl, $C_1$–$C_{10}$ alkyl, $C_2$–$C_{10}$ alkenyl, $C_2$–$C_{10}$ alkynyl, $C_3$–$C_{10}$ cycloalkyl, saturated $C_5$–$C_{10}$ heteroaryl, $C_5$–$C_{10}$ aryl-$C_1$–$C_{10}$ alkyl, $C_5$–$C_{10}$ heteroaryl-$C_1$–$C_{10}$ alkyl, $COR_7$, $CO_2R_7$, $CONR_7R_8$, $SO_2NR_7R_8$, said aryl, heteroaryl, alkyl, alkenyl, and cycloalkyl optionally substituted with 1 to 3 groups of $R_s$;

$R_7$ and $R_8$ independently are H, hydroxy, $C_1$–$C_{10}$ alkyl, $C_2$–$C_{10}$ alkenyl, $C_2$–$C_{10}$ alkynyl, $C_3$–$C_{10}$ cycloalkyl, $C_5$–$C_{10}$ aryl, $C_5$–$C_{10}$ heteroaryl, said aryl, heteroaryl, alkyl, alkenyl, and cycloalkyl optionally substituted with 1 to 3 groups of $R_s$;

$R_s$ represents a member selected from the group consisting of halo, cyano, nitro, trihalomethyl, carbamoyl, hydroxy, $OCF_3$, acyl, aryl, heteroaryl, $S(O)R_8$, =$N(OR_8)$, $SO_2R_8$, $COOR_8$, —$CONR_7R_8$, —$C_1$–$C_6$alkylCONR_7R_8$, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, $NR_7R_8$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, aryl$C_1$–$C_6$alkylcarboxy, —$NR_7CO_2R_8$, —$NR_7COR_8$, —$NR_7CO_2R_8$, —$NR_7SO_2R_8$, —$CONR_7R_8$, —$SO_2NR_7R_8$, —$OCONR_7R_8$, —$C_1$–$C_6$alkylaminoCONR_7R_7R_8$, aryl$C_1$–$C_6$alkylcarbonylamino, tetrahydrofuryl, morpholinyl, piperazinyl, or a saturated or partial saturated cyclic 5,6 or 7 membered amine or lactam; said aryl, land heteroaryl optionally substituted with 1 to 3 groups of halo or $C_1$–$C_6$alkyl; wherein $R_7$ and $R_8$ are defined as above.

2. A compound according to claim 1, wherein X is oxygen.

3. A compound according to claim 1, wherein A is —C(O)—.

4. A compound according to claim 1, wherein B is $NR_6$, wherein $R_6$ is hydrogen, $C_1$–$C_6$ alkyl.

5. A compound according to claim 1, wherein G is $C_3$–$C_{10}$ cycloalkyl, $C_4$–$C_6$ cycloalkenyl, saturated $C_3$–$C_{10}$ heterocyclyl.

6. A compound according to claim 5, wherein cycloalkyl is cyclohexyl.

7. A compound according to claim 1, wherein $R_1$ is hydrogen.

8. A compound according to claim 1, wherein $R_3$ and $R_4$ are optionally substituted $C_1$–$C_{10}$ alkyl, and $C_5$–$C_{10}$aryl-$C_1$–$C_{10}$ alkyl.

9. A compound according to claim 7, wherein alkyl is n-butyl or iso-butyl, arylalkyl is 3,5-dimethoxybenzyl.

10. A compound according to claim 1, wherein $R_5$ is optionally substituted alkyl.

11. A compound according to claim 1 which is selected from the group consisting of:

Methyl[1-cyclohexylcarbamoyl-4-benzyl-6-(S)-isobutyl-5-oxo-piperazin-2-yl]-acetate;

[1-Cyclohexylcarbamoyl-4-benzyl-6-(S)-isobutyl-5-oxo-piperazin-2-yl]-acetic acid;

N-Tetrahydrofurfuryl[1-cyclohexylcarbamoyl-4-benzyl-6-(S)-isobutyl-5-oxo-piperazin-2-yl]-acetamide;

N-Methyl[1-cyclohexylcarbamoyl-4-(3,5-dimethoxybenzyl)-6-(S)-isobutyl-piperazin-2-yl]-acetamide;

[1-Cyclohexylcarbamoyl-4-benzyl-6-(S)-benzyl-5-oxo-piperazin-2-yl]-acetic acid;

N-Methyl[1-cyclohexylcarbamoyl-4-benzyl-6-(S)-benzyl-5-oxo-piperazin-2-yl]-acetamide;

N-Methyl[1-cyclohexylcarbamoyl-4-(4-methoxybenzyl)-6-(S)-methylcarbamoyl-3-oxo-piperazin-2-yl]-acetamide;

N-Tetrahydrofurfuryl(R)-[1-cyclohexylcarbamoyl-4-(3,5-dimethoxybenzyl)-6-(S)-isobutyl-5-oxo-piperazin-2-yl]-acetamide;

N-Tetrahydrofurfuryl(S)-[1-cyclohexylcarbamoyl-4-(3,5-dimethoxybenzyl)-6-(S)-isobutyl-5-oxo-piperazin-2-yl]-acetamide;

N-Tetrahydrofurfuryl(R)-[1-cyclohexylcarbamoyl-4-cyclohexylmethyl-6-(S)-isobutyl-5-oxo-piperazin-2-yl]-acetamide;

N-Tetrahydrofurfuryl(S)-[1-cyclohexylcarbamoyl-4-cyclohexylmethyl-6-(S)-isobutyl-5-oxo-piperazin-2-yl]-acetamide;
N-Butyl(R)-[1-cyclohexylcarbamoyl-4-(3-pyridylmethyl)-6-(S)-isobutyl-5-oxo-piperazin-2-yl]-acetamide;
N-Butyl(S)-[1-cyclohexylcarbamoyl-4-(3-pyridylmethyl)-6-(S)-isobutyl-5-oxo-piperazin-2-yl]-acetamide;
N-Butyl(R)-[1-cyclohexylcarbamoyl-4-(3,4-dimethoxybenzyl)-6-(S)-isobutyl-5-oxo-piperazin-2-yl]-acetamide;
N-Butyl(S)-[1-cyclohexylcarbamoyl-4-(3,4-dimethoxybenzyl)-6-(S)-isobutyl-5-oxo-piperazin-2-yl]-acetamide;
[1-cyclohexylcarbamoyl-4-(3,4-dimethoxybenzyl)-6-(S)-isobutyl-5-oxo-piperazin-2-yl]-acetic acid;
(R)-[1-cyclohexylcarbamoyl-4-(3,4-dimethoxybenzyl)-6-(S)-isobutyl-5-oxo-piperazin-2-yl]-acetic acid;
(S)-[1-cyclohexylcarbamoyl-4-(3,4-dimethoxybenzyl)-6-(S)-isobutyl-5-oxo-piperazin-2-yl]-acetic acid;
N-Methyl(R)-[1-(1-piperidylcarbamoyl)-4-(3,4-dimethoxybenzyl)-6-(S)-isobutyl-5-oxo-piperazin-2-yl]-acetamide;
N-Methyl(S)-[1-(1-piperidylcarbamoyl)-4-(3,4-dimethoxybenzyl)-6-(S)-isobutyl-5-oxo-piperazin-2-yl]-acetamide;
N-Tetrahydrofurfuryl(R)-[1-cyclohexylcarbamoyl-4-(3,4-dimethoxybenzyl)-6-(S)-isobutyl-5-oxo-piperazin-2-yl]-acetamide;
N-Tetrahydrofurfuryl(S)-[1-cyclohexylcarbamoyl-4-(3,4-dimethoxybenzyl)-6-(S)-isobutyl-5-oxo-piperazin-2-yl]-acetamide;
N-Tetrahydrofurfuryl(R)-[1-cyclohexylcarbamoyl-4-(4-dimethylaminobenzyl)-6-(S)-isobutyl-5-oxo-piperazin-2-yl]-acetamide;
N-Tetrahydrofurfuryl(S)-[1-cyclohexylcarbamoyl-4-(4-dimethylaminobenzyl)-6-(S)-isobutyl-5-oxo-piperazin-2-yl]-acetamide;
Methyl[1-cyclohexylcarbamoyl-4-(3,5-dimethoxybenzyl)-6-(S)-isobutyl-5-oxo-piperazin-2-yl]-acetate;
N-Methyl(R)-[1-cyclohexylmethylcarbamoyl-4-(3,5-dimethoxybenzyl)-6-(S)-isobutyl-5-oxo-piperazin-2-yl]-acetamide;
N-Methyl(S)-[1-cyclohexylmethylcarbamoyl-4-(3,5-dimethoxybenzyl)-6-(S)-isobutyl-5-oxo-piperazin-2-yl]-acetamide;
N-Methyl(R)-[1-cyclohexylcarbamoyl-4-benzyl-6-(S)-isobutyl-5-oxo-piperazin-2-yl]-acetamide;
N-Methyl(S)-[1-cyclohexylcarbamoyl-4-benzyl-6-(S)-isobutyl-5-oxo-piperazin-2-yl]-acetamide;
N-Methyl(R)-[1-cyclopentylcarbamoyl-4-(3,5-dimethoxybenzyl)-6-(S)-isobutyl-5-oxo-piperazin-2-yl]-acetamide;
N-Methyl(S)-[1-cyclopentylcarbamoyl-4-(3,5-dimethoxybenzyl)-6-(S)-isobutyl-5-oxo-piperazin-2-yl]-acetamide;
N-Methyl[1-cyclohexylcarbamoyl-4-(3,5-dimethoxybenzyl)-6-(S)-isobutyl-5-oxo-piperazin-2-yl]-acetamide;
N-Methyl(R)-[1-cyclohexylcarbamoyl-4-(3,5-dimethoxybenzyl)-6-(S)-isobutyl-5-oxo-piperazin-2-yl]-acetamide;
N-Methyl(S)-[1-cyclohexylcarbamoyl-4-(3,5-dimethoxybenzyl)-6-(S)-isobutyl-5-oxo-piperazin-2-yl]-acetamide;
N-Butyl[1-cyclohexylcarbamoyl-4-(3,5-dimethoxybenzyl)-6-(S)-isobutyl-5-oxo-piperazin-2-yl]-acetamide;
N-Butyl(R)-[1-cyclohexylcarbamoyl-4-(3,5-dimethoxybenzyl)-6-(S)-isobutyl-5-oxo-piperazin-2-yl]-acetamide;
N-Butyl(S)-[1-cyclohexylcarbamoyl-4-(3,5-dimethoxybenzyl)-6-(S)-isobutyl-5-oxo-piperazin-2-yl]-acetamide;
N-Butyl(R)-[1-cyclohexylcarbamoyl-4-cyclohexylmethyl-6-(S)-isobutyl-5-oxo-piperazin-2-yl]-acetamide;
N-Butyl(S)-[1-cyclohexylcarbamoyl-4-cyclohexylmethyl6-(S)-isobutyl-5-oxo-piperazin-2-yl]-acetamide;
N-Methyl[1-cyclohexylcarbamoyl-4-cyclohexylmethyl-6-(S)-isobutyl-5-oxo-piperazin-2-yl]-acetamide;
N-Methyl[1-cyclohexylcarbamoyl-4-(3,5-dimethoxybenzyl)-6-(S)-butyl-5-oxo-piperazin-2-yl]-acetamide;
N-Ethyl[1-cyclohexylcarbamoyl-4-(3,5-dimethoxybenzyl)-6-(S)-isobutyl-5-oxo-piperazin-2-yl]-acetamide;
N-(2-Hydroxyethyl)[1-cyclohexylcarbamoyl-4-(3,5-dimethoxybenzyl)-6-(S)-isobutyl-5-oxo-piperazin-2-yl]-acetamide.

12. A pharmaceutical composition which comprises a compound according to any of claims 1–11 or a pharmaceutical acceptable salt thereof and a pharmaceutically acceptable carrier or excipient.

13. A process for preparing a pharmaceutical composition which comprises admixing a compound according to any of claims 1–11 or a pharmaceutical acceptable salt thereof with a pharmaceutically acceptable carrier or excipient.

14. A method for the rent of a condition selected from the group consisting of Type I diabetes, Type II diabetes, atherosclerosis, hyperglycemia, hyperlipidemia, obesity, syndrome X, insulin resistance, hypertension, heart failure and cardiovascular disease by administering to a mammal a the therapeutically effective amount of a compound of formula 1:
wherein:

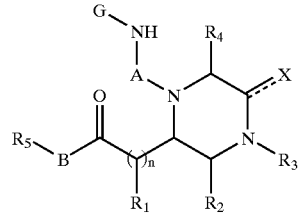

Formula (I)

X is H, O, S;
A is —C(O)—, —S(O)m—;
B is O, S, $NR_6$, wherein $R_6$ is H, $C_1$–$C_6$ alkyl, $C_2$–$C_6$ alkenyl and $C_2$–$C_6$ alkynyl and $C_3$–$C_6$ cycloalkyl;
n is 0 or 1;
m is 1 or 2;
G is $C_3$–$C_{10}$ cycloalkyl, $C_4$–$C_{10}$ cycloalkenyl, saturated $C_3$–$C_{10}$ heterocyclyl, $C_3$–$C_{10}$ cycloalkyl-$C_1$–$C_3$ alkyl, $C_4$–$C_{10}$ cycloalkenyl-$C_1$–$C_3$ alkyl, saturated $C_3$–$C_{10}$ heterocyclyl-$C_1$–$C_3$ alkyl, said cycloalkyl, cycloalkenyl, heterocyclyl and alkyl optionally substituted with 1 to 3 groups of $R_5$, wherein heterocyclyl contains 1 to 4 heteroatoms which may be nitrogen, sulfur or oxygen atom;
$R_1$ is hydrogen, hydroxy, thio, nitro, cyano, azido, amino, trifluoromethyl, trifluoromethoxy, $C_1$–$C_6$ alkyl, $C_1$–$C_6$ alkyloxy, $C_1$–$C_6$ alkylthio, $C_1$–$C_6$ alkylamino, $C_1$–$C_6$ alkenyl, $C_1$–$C_6$ alkenyloxy, $C_1$–$C_6$ alkenylamino, $C_3$–$C_8$ cycloalkyl, $C_3$–$C_8$ cycloalkyloxy, $C_3$–$C_8$ cycloalkylamino, $C_3$–$C_8$ cycloalkylthio, $C_1$–$C_6$ alkylcarbonylamino, $C_3$–$C_8$ cycloalkylcarbonylamino, $C_5$–$C_{10}$ aryl, $C_5$–$C_{10}$ heteroaryl or $C_5$–$C_{10}$ saturated heteroaryl; said aryl, heteroaryl, alkyl, alkenyl, and cycloalkyl optionally substituted with 1 to 3 groups of $R_s$;

$R_2$, $R_3$ and $R_5$ independently are H, trifluoromethyl, $C_5$–$C_{10}$ aryl, $C_5$–$C_{10}$ heteroaryl, $C_1$–$C_{10}$ alkyl, $C_2$–$C_{10}$ alkenyl, $C_2$–$C_{10}$ alkynyl, $C_3$–$C_{10}$ cycloalkyl, saturated $C_5$–$C_{10}$ heteroaryl, $C_5$–$C_{10}$ aryl-$C_1$–$C_{10}$ alkyl, $C_5$–$C_{10}$ heteroaryl-$C_1$–$C_{10}$ alkyl, $COR_7$, $CO_2R_7$, $CONR_7R_8$, $SO_2NR_7R_8$, said aryl, heteroaryl, alkyl, alkenyl, and cycloalkyl optionally substituted with 1 to 3 groups of $R_s$;

$R_4$ is selected from the group consisting of trifluoromethyl, $C_5$–$C_{10}$ aryl, $C_5$–$C_{10}$ heteroaryl, $C_1$–$C_{10}$ alkyl, $C_2$–$C_{10}$ alkenyl, $C_2$–$C_{10}$ alkynyl, $C_3$–$C_{10}$ cycloalkyl, saturated $C_5$–$C_{10}$ heteroaryl, $C_5$–$C_{10}$ aryl-$C_1$–$C_{10}$ alkyl, $C_5$–$C_{10}$ heteroaryl-$C_1$–$C_{10}$ alkyl, $COR_7$, $CO_2R_7$, $CONR_7R_8$, $SO_2NR_7R_8$, said aryl, heteroaryl, alkyl, alkenyl, and cycloalkyl optionally substituted with 1 to 3 groups of $R_s$;

$R_7$ and $R_8$ independently are H, hydroxy, $C_1$–$C_{10}$ alkyl, $C_2$–$C_{10}$ alkenyl, $C_2$–$C_{10}$ alkynyl, $C_3$–$C_{10}$ cycloalkyl, $C_5$–$C_{10}$ aryl, $C_5$–$C_{10}$ heteroaryl, said aryl, heteroaryl, alkyl, alkenyl, and cycloalkyl optionally substituted with 1 to 3 groups of $R_s$;

$R_s$ represents a member selected from the group consisting of halo, cyano, nitro, trihalomethyl, carbamoyl, hydroxy, $OCF_3$, acyl, aryl, heteroaryl, $S(O)R_8$, $=N(OR_8)$, $SO_2R_8$, $COOR_8$, $—CONR_7R_8$, $—C_1$–$C_6$alkylCONR$_7$R$_8$, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, $NR_7R_8$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, aryl$C_1$–$C_6$alkylcarboxy, $—NR_7CO_2R_8$, $—NR_7COR_8$, $—NR_7CO_2R_8$, $—NR_7SO_2R_8$, $—CONR_7R_8$, $—SO_2NR_7R_8$, $—OCONR_7R_8$, $—C_1$–$C_6$alkylaminoCONR$_7$R$_8$, aryl$C_1$–$C_6$alkylcarbonylamino, tetrahydrofuryl, morpholinyl, piperazinyl, or a saturated or partial saturated cyclic 5,6 or 7 membered amine or lactam; said aryl, and heteroaryl optionally substituted with 1 to 3 groups of halo or $C_1$–$C_6$alkyl; wherein $R_7$ and $R_8$ are defined as above.

* * * * *